(12) United States Patent
Nazzaro

(10) Patent No.: US 11,819,454 B2
(45) Date of Patent: Nov. 21, 2023

(54) INTRAOCULAR INJECTOR

(71) Applicant: Inflammasome Therapeutics, Inc., Newton, MA (US)

(72) Inventor: Martin Nazzaro, Quincy, MA (US)

(73) Assignee: Inflammasome Therapeutics, Inc., Newton, MA (US)

( * ) Notice: Subject to any disclaimer, the term of this patent is extended or adjusted under 35 U.S.C. 154(b) by 138 days.

(21) Appl. No.: 17/497,466

(22) Filed: Oct. 8, 2021

(65) Prior Publication Data

US 2022/0168141 A1 Jun. 2, 2022

Related U.S. Application Data

(60) Provisional application No. 63/089,931, filed on Oct. 9, 2020.

(51) Int. Cl.
*A61F 9/00* (2006.01)
*A61M 5/32* (2006.01)
*A61M 5/46* (2006.01)

(52) U.S. Cl.
CPC ......... *A61F 9/0017* (2013.01); *A61M 5/3286* (2013.01); *A61M 5/46* (2013.01); *A61M 2210/0612* (2013.01)

(58) Field of Classification Search
CPC ............ A61F 9/0017; A61F 2250/0068; A61F 9/00781; A61F 2250/0067; A61F 2/14; A61F 9/007; A61F 9/0008; A61F 2/0063; A61F 2/0095; A61F 2/011; A61F 2/95; A61F 2/167; A61M 5/3286; A61M 5/46; A61M 2210/0612; A61M 5/31566; A61M 37/0069; A61M 2205/04; A61M 5/158; A61M 5/329; A61M 2005/1585; A61M 5/3293; A61M 5/34; A61M 5/145; A61K 9/0051; A61P 27/02; A61B 5/6821; A61B 5/6861; A61B 17/3468; A61B 17/00
See application file for complete search history.

(56) References Cited

U.S. PATENT DOCUMENTS

| | | | |
|---|---|---|---|
| 4,373,526 A * | 2/1983 | Kling | A61M 5/46 604/117 |
| 4,446,647 A * | 5/1984 | Kahl | A01K 83/02 43/36 |
| 2007/0293873 A1* | 12/2007 | Chang | A61K 9/0051 606/107 |
| 2009/0281520 A1* | 11/2009 | Highley | A61M 5/322 604/63 |

(Continued)

*Primary Examiner* — Nicholas J. Weiss
*Assistant Examiner* — Brandon W. Levy
(74) *Attorney, Agent, or Firm* — Foley Hoag LLP; David P. Halstead; Stephen J. Kenny

(57) ABSTRACT

Assemblies for and methods of intraocular injection. An injector assembly includes a housing defining an internal chamber and having a slot on an external surface thereof; a cannula needle having a lumen and a cutout on an outer surface; a flexible arm having a proximal end affixed to the outer surface of the cannula needle and a distal end having a hook such that the hook is disposed within the cutout; a pushrod slidably disposed within the lumen; and a latch slidably disposed in the slot of the housing, the latch coupled to the pushrod such that translation of the latch causes translation of the pushrod to thereby eject an implant disposed within the lumen between the hook and pushrod.

16 Claims, 30 Drawing Sheets

(56) References Cited

U.S. PATENT DOCUMENTS

| | | | |
|---|---|---|---|
| 2011/0098675 A1* | 4/2011 | Schmalz | A61M 37/0069 604/60 |
| 2013/0253438 A1* | 9/2013 | Badawi | A61F 9/007 604/239 |
| 2017/0224928 A1* | 8/2017 | Högdahl | A61M 5/3204 |
| 2017/0259009 A1* | 9/2017 | Sjökvist | A61M 5/3293 |
| 2019/0200977 A1* | 7/2019 | Shelton, IV | A61B 17/068 |

* cited by examiner

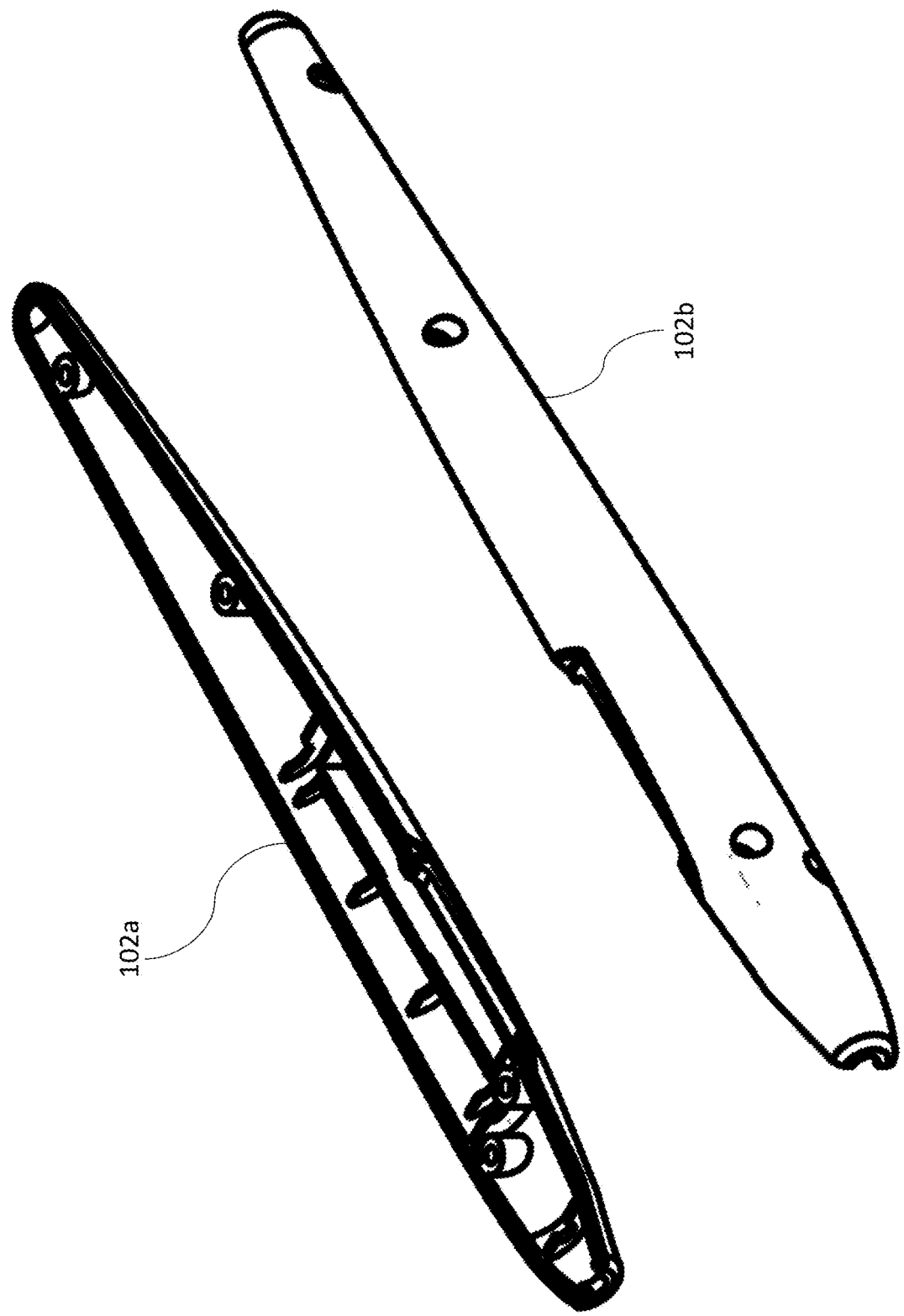

SECTION A-A
SCALE 1 : 1

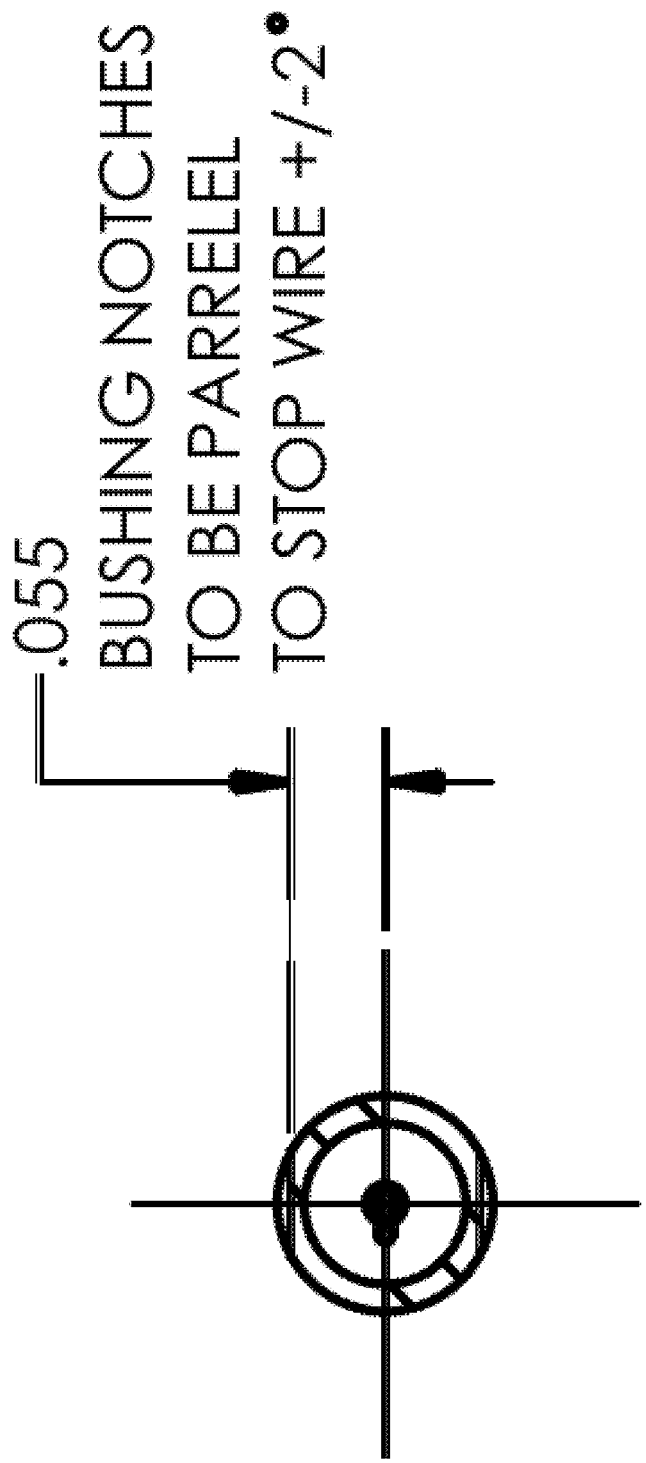

INTRAOCULAR INJECTOR

CROSS-REFERENCE TO RELATED APPLICATION

This application claims the benefit of U.S. Provisional Patent Application No. 63/089,931, filed Oct. 9, 2020, which is hereby incorporated by reference in its entirety.

FIELD OF THE INVENTION

Embodiments of the present disclosure relate to intraocular injectors.

BACKGROUND

The human eye is a highly evolved and complex sensory organ. Damage to any of its essential structures can result in impairment of vision. Treatments of various eye conditions and diseases often consist of applying doses of appropriate medications in aqueous suspension solutions or ointments. While such treatments are satisfactory for conditions that require only one or a few applications of the medicinal agents, certain conditions require more frequent doses and such treatments are inconvenient to patients. In contrast, ophthalmic medicinal agents in solid implant forms allow a high weight of drug per administered volume. This is particularly advantageous when a large amount of drug must be administered over a period of time per dose or when the volume is constrained, as in intraocular injections. Additionally, the solid state also renders the compound less sensitive to solution-mediated chemical degradation.

Direct injection into a sensitive and delicate structure like the eye has certain challenges and attendant difficulties. There are a number of procedures and devices that have been developed for the controlled injection of an implant into a tissue, such as an eye. However, improved procedures and devices would be beneficial.

BRIEF SUMMARY

According to embodiments of the present disclosure, assemblies for and methods of intraocular injection are provided. In various embodiments, an injector assembly includes a housing defining an internal chamber. The housing has a proximal end and a distal end including a distal opening. The housing has a slot on an external surface thereof between the proximal end and distal end. The injector assembly further includes a cannula needle having a proximal end disposed within the housing and extending at least partially through the distal opening to a distal end. The cannula needle has a lumen extending therethrough. The cannula needle has a distal bevel at the distal end and a proximal opening at the proximal end. The cannula needle has a cutout on an outer surface. The injector assembly further includes a flexible arm having a proximal end and a distal end, where the proximal end of the flexible arm is affixed to the outer surface of the cannula needle and the distal end of the flexible arm has a hook. In various embodiments, the hook prevents the payload (e.g., an implant) from falling out of the cannula needle prematurely. The hook is disposed within the cutout. The injector assembly further includes a pushrod slidably disposed within the lumen and the pushrod extends at least partially through the distal end of the cannula needle. The injector assembly further includes a latch slidably disposed in the slot of the housing. The latch is coupled to the pushrod such that translation of the latch causes translation of the pushrod.

In various embodiments, a needle subassembly includes a cannula needle having a proximal end, a distal end, and a lumen extending therethrough. The cannula needle has a distal bevel at the distal end and a proximal opening at the proximal end. The cannula needle has a cutout in an outer surface. The needle subassembly further includes a flexible arm having a proximal end and a distal end, where the proximal end of the flexible arm is affixed to the outer surface of the cannula needle and the distal end of the flexible arm has a hook. The hook is disposed within the cutout. The needle subassembly further includes a pushrod slidably disposed within the lumen and the pushrod extends at least partially through the distal end of the cannula needle. The needle subassembly further includes an implant disposed proximal to the hook and distal to the pushrod.

In various embodiments, a method of inserting an implant into an eye includes providing an injector assembly, inserting the distal end of the cannula needle into an eye, positioning the cannula needle at a target location within the eye, sliding the latch towards the distal end of the housing to thereby advance the pushrod against the implant, displacing the hook, until the implant is ejected from the needle cannula.

BRIEF DESCRIPTION OF THE SEVERAL VIEWS OF THE DRAWINGS

FIGS. 2B-2G illustrates various mechanical drawings of an intraocular injector housing in accordance with an embodiment of the present disclosure.

FIGS. 6A-6C illustrates various mechanical drawings of a needle subassembly with needle stop in accordance with an embodiment of the present disclosure.

DETAILED DESCRIPTION

Figure 1A:
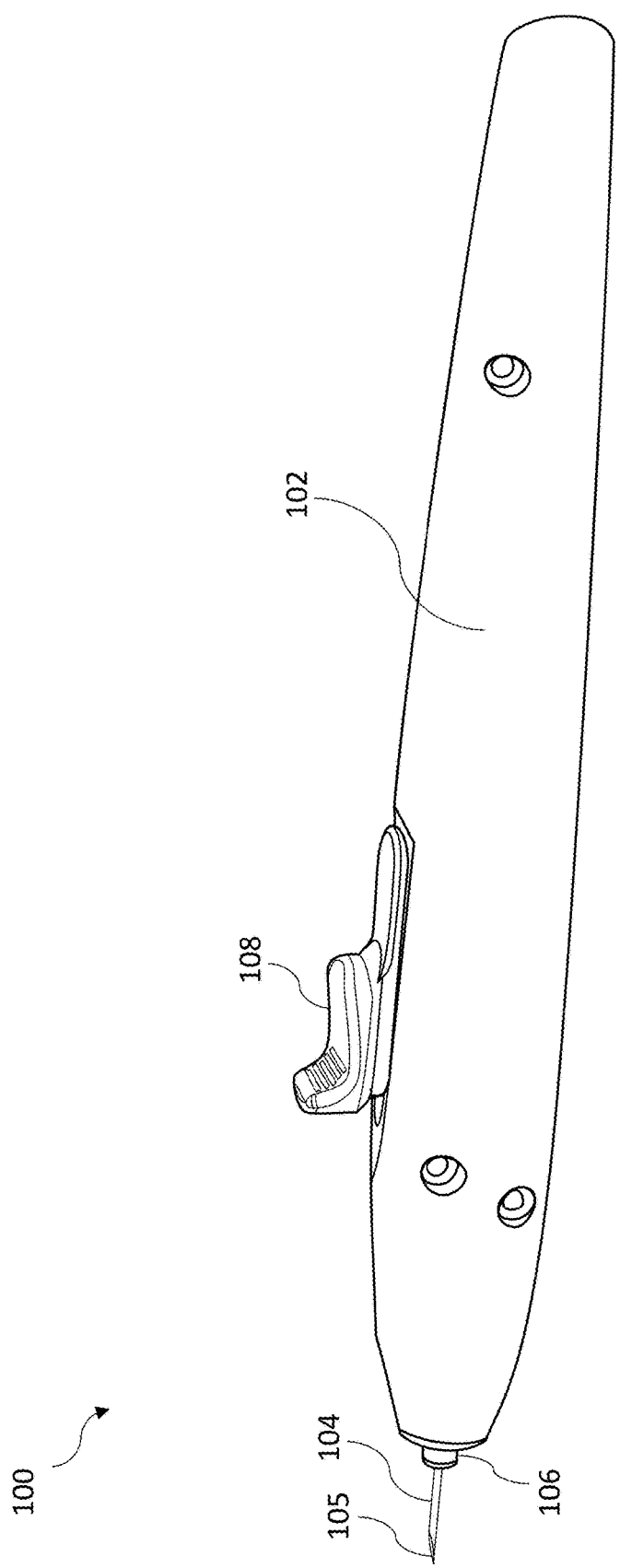
FIGS. 1A-1C illustrate an intraocular injector assembly in accordance with an embodiment of the present disclosure.

The assemblies, subassemblies, and methods described herein provide an injector device capable of delivering an implant into a tissue (e.g., ocular tissue). Traditional injector devices are uncomfortable to use due to a number of factors including size of the device and ergonomics of the control mechanism (e.g., button) that provides for ejection of an implant to be delivered. For example, the force to eject the implant may be enough that the process of ejection is uncomfortable for an average user (e.g., a healthcare provider) and/or the position of the ejection button makes use of the device uncomfortable for the user. Moreover, many commercial injectors have overly-complicated mechanisms which may cause issues at any time during the procedure, including during the critical time frame when the injector is inserted into the vitreous chamber of the eye, but prior to ejection of the implant at the target location. Additionally, many commercial injectors have issues with the payload (e.g., an implant) falling out of the cannula needle prior to insertion into the eye, which results in expensive monetary losses. Moreover, due to the small size of the payload, the physician may not notice if the payload is prematurely ejected (e.g., falls out) out of the device and may proceed with piercing the tissue thereby delivering nothing.

In certain embodiments, the injector device is fitted with a slidable latch coupled to a pushrod and a flexible arm having a hook that is disposed within a cutout of a needle cannula to thereby prevent premature ejection of the implant. When the latch is pushed forward by the force of a user's finger, the pushrod advances an implant through the cannula needle, displacing the hook out of the cutout, until the implant is ejected out of the cannula needle. It will be understood by one of ordinary skill in the art that the device and method described herein can be adapted and modified for other suitable applications and that such other additions and modifications will not depart from the scope hereof.

FIGS. 1A-1D illustrate an intraocular injector assembly 100 in accordance with an embodiment of the present disclosure. In various embodiments, the injector assembly 100 includes a housing 102. In various embodiments, the housing 102 may be made from one or more (e.g., two) components. For example, in the embodiment shown in FIGS. 1A-1D, the housing 102 includes two halves affixed to one another. In various embodiments, the housing 102 may be made from a polymer. In various embodiments, the housing 102 may be made by injection molding or 3D printing. In various embodiments, proximal and distal may be defined relative to the user such that distal is away from the user and proximal is closer to the user. Alternatively, in various embodiments, proximal and distal may be defined relative to the patient such that proximal is away from the user and distal is closer to the user. In various embodiments, the housing 102 includes a distal opening from which a cannula 104 needle may extend and a proximal end near the user.

In various embodiments, the cannula needle 104 extends at least partially out of the distal opening of the housing 102 to a distal end 105 which includes a beveled (e.g., sharpened) edge configured to pierce a tissue (e.g., sclera, conjunctival tissue, etc.). In various embodiments, the cannula needle 104 is fixed relative to the housing 102; optionally, the cannula needle 104 can be adjustable in length relative to the housing 102 (e.g. the needle 104 can be retractable within the housing 102). In various embodiments, the beveled edge may have an angle from the horizontal (i.e., longitudinal axis of cannula needle) of about 5 degrees to about 35 degrees. Preferably, the bevel has an angle from the horizontal of about 11 degrees. The angle can be constant, resulting in a linear edge, or non-linear with various points of inflection along the outer face of the needle. In various embodiments, as described with respect to FIG. 2, the cannula needle 104 may be housed at least partially inside the housing 102. In various embodiments, the cannula needle may have a length of about 20 mm to about 500 mm suitable for ejecting an implant at a target location within the eye (e.g., the vitreous chamber). In various embodiments, the length of the cannula needle may be any suitable length such that the cannula needle may be inserted at least 8 mm into the eye.

In various embodiments, the injector assembly 100 may further include a needle stop 106 positioned at the distal opening of the housing 102. The needle stop 106 may extend at least partially out of the distal opening of the housing 102 and be configured to indicate to a user an optimal insertion depth for the cannula needle. In various embodiments, the optimal insertion depth of the cannula needle 104 may be about 3 mm to about 100 mm. Preferably, the optimal insertion depth may be about 3 mm to about 10 mm. Most preferably, the optimal insertion depth may be about 3 mm to about 8 mm. In various embodiments, the size of the cannula needle 104 may be about 21 gauge to about 28 gauge. Preferably, the size of the cannula needle 104 may be about 22 gauge to about 27 gauge.

In various embodiments, the injector assembly 100 includes a latch 108 extending from the housing 102 and configured to translate within a slot 109 formed in the housing 102. In various embodiments, as described in more detail below, the latch 108 is coupled to a pushrod configured to advance an implant contained within the cannula needle 104 until the implant is ejected from the cannula needle 104. In various embodiments, the latch 108 may be ergonomically designed to fit a particular finger of a user, such as the index finger. The latch 108 can move relative to the housing with a translational movement only, or can be depressed downward, and thereafter moved in a translational manner to advance/retract the pushrod.

Figure 1B:
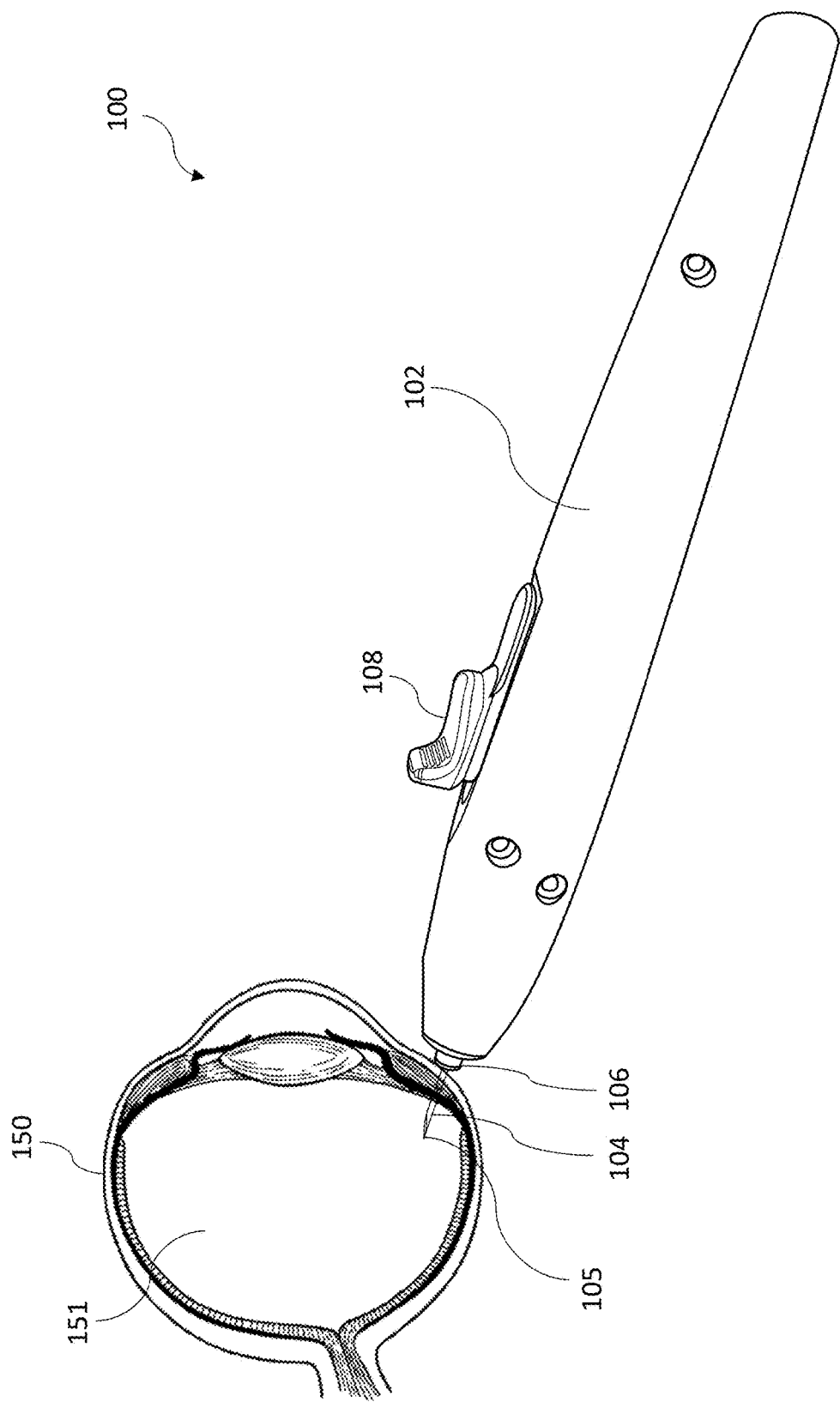
Figure 1C:
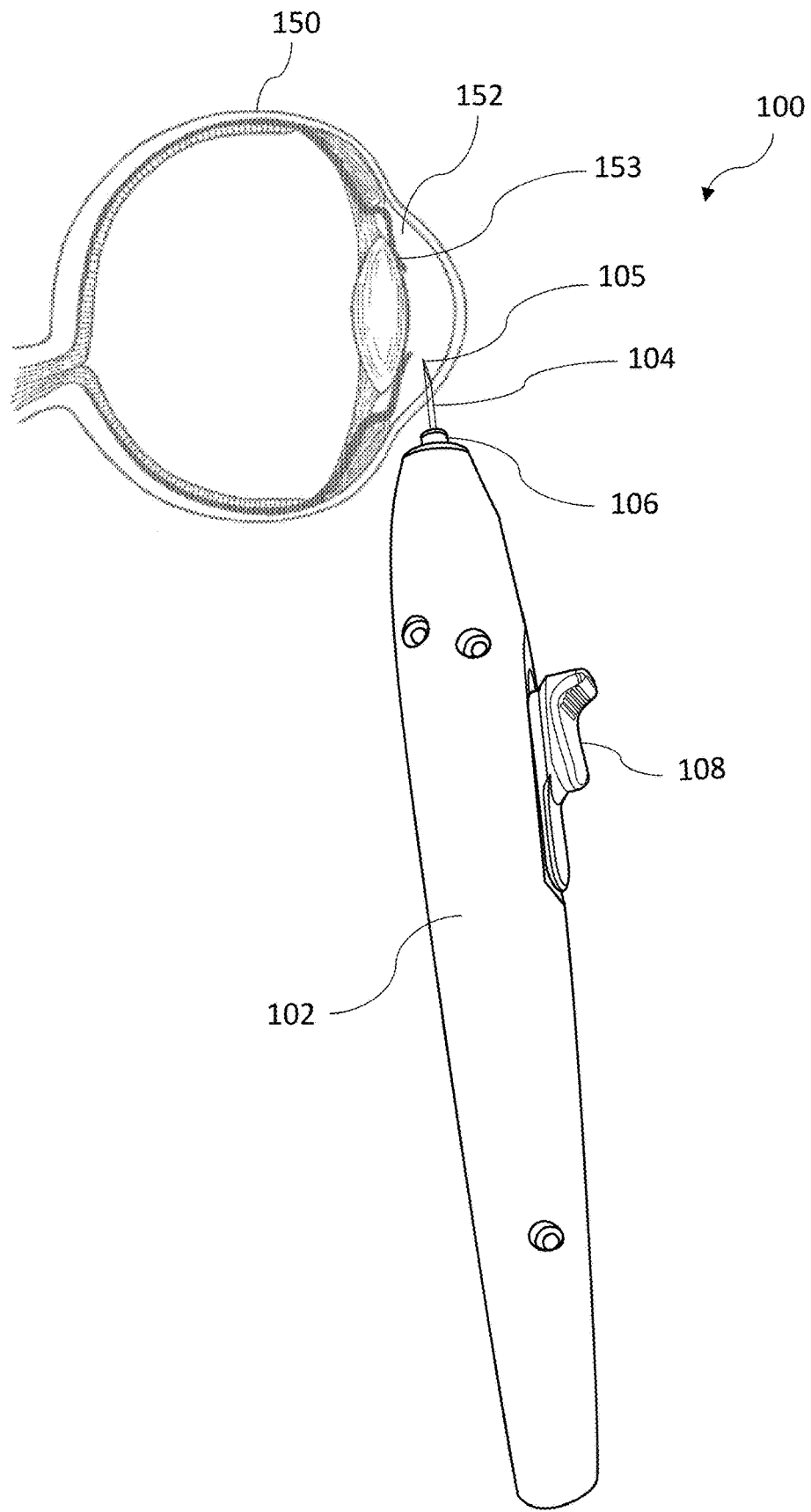
Figure 1D:
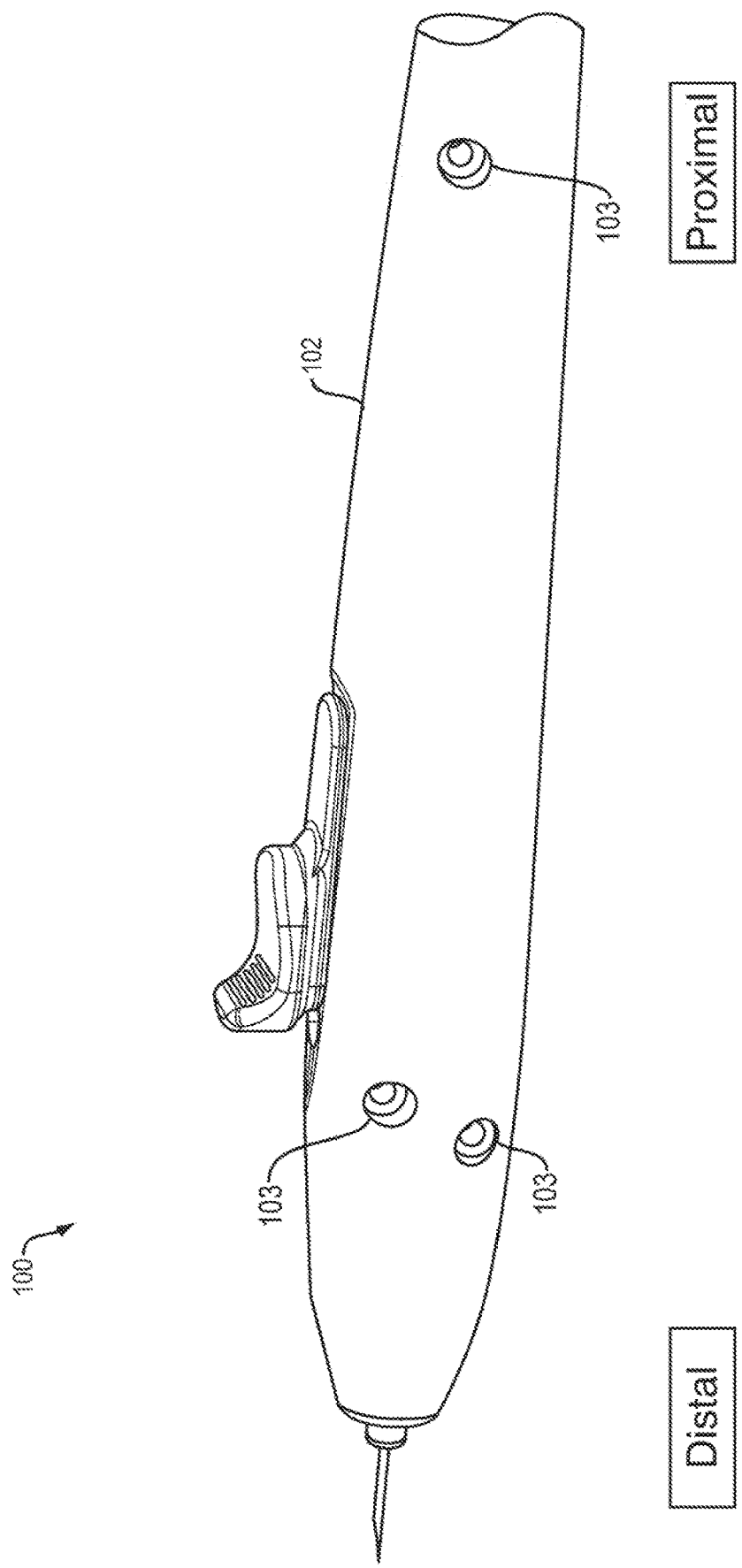
FIG. 1D illustrates a 3D model of an intraocular injector assembly in accordance with an embodiment of the present disclosure.
Figure 2A:
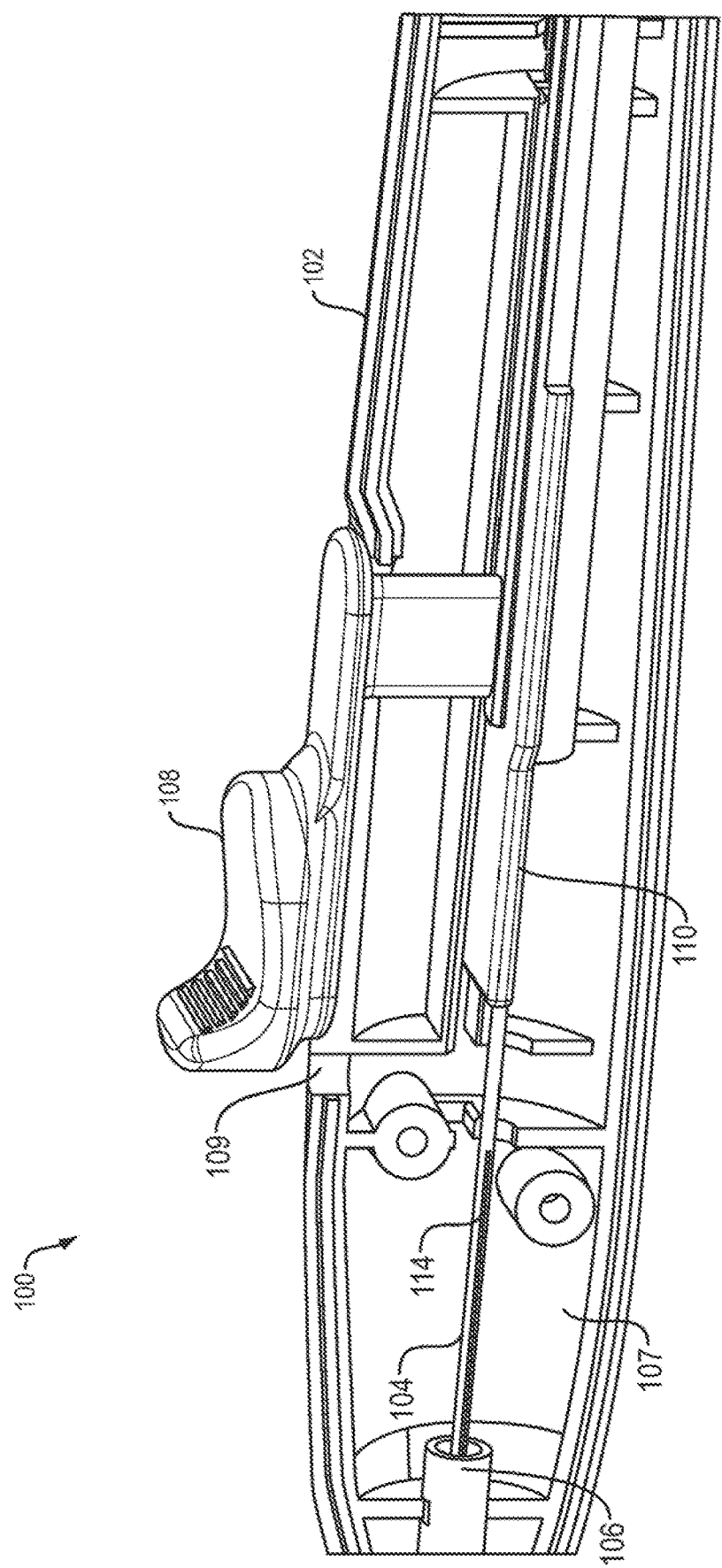
FIG. 2A illustrates a cross-section of an intraocular injector assembly in accordance with an embodiment of the present disclosure.
Figure 2C:
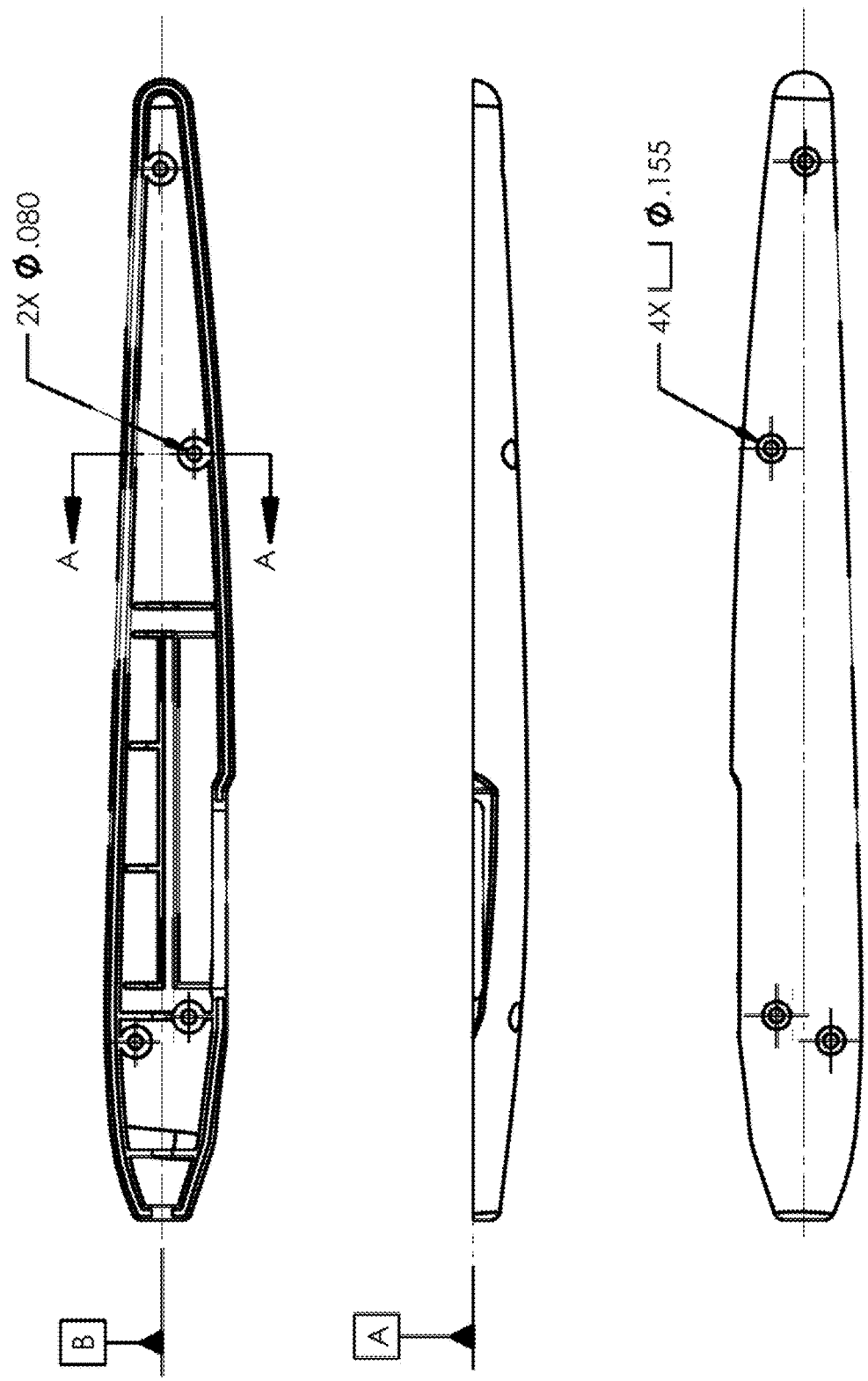
Figure 2D:
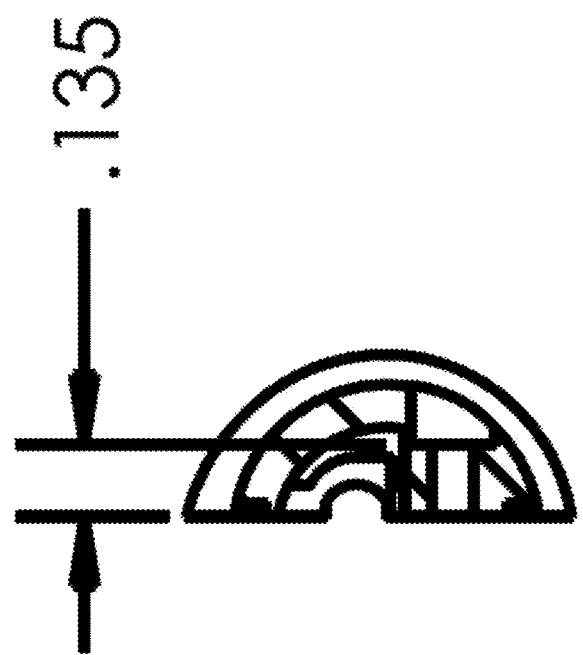
Figure 2E:
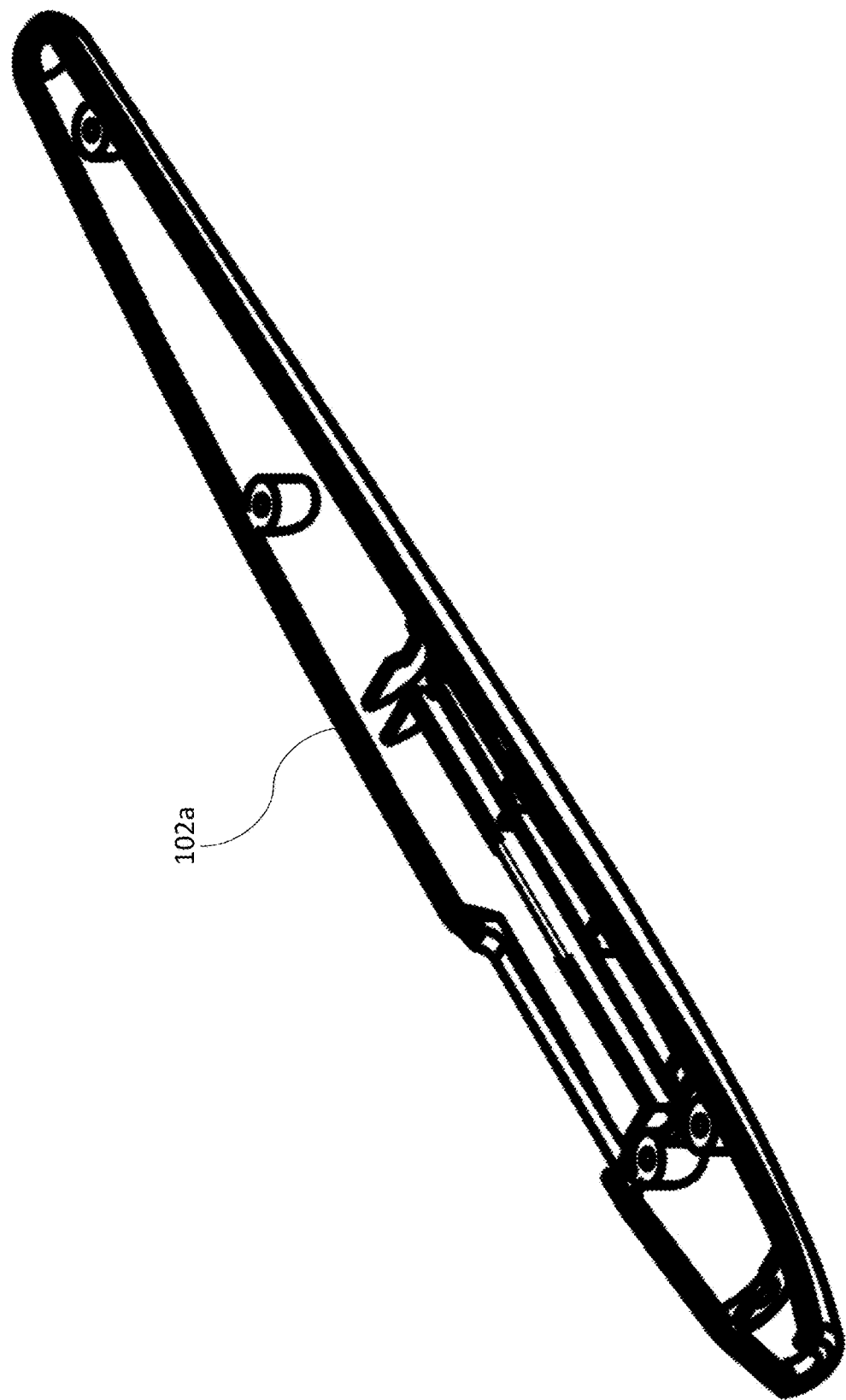
Figure 2F:
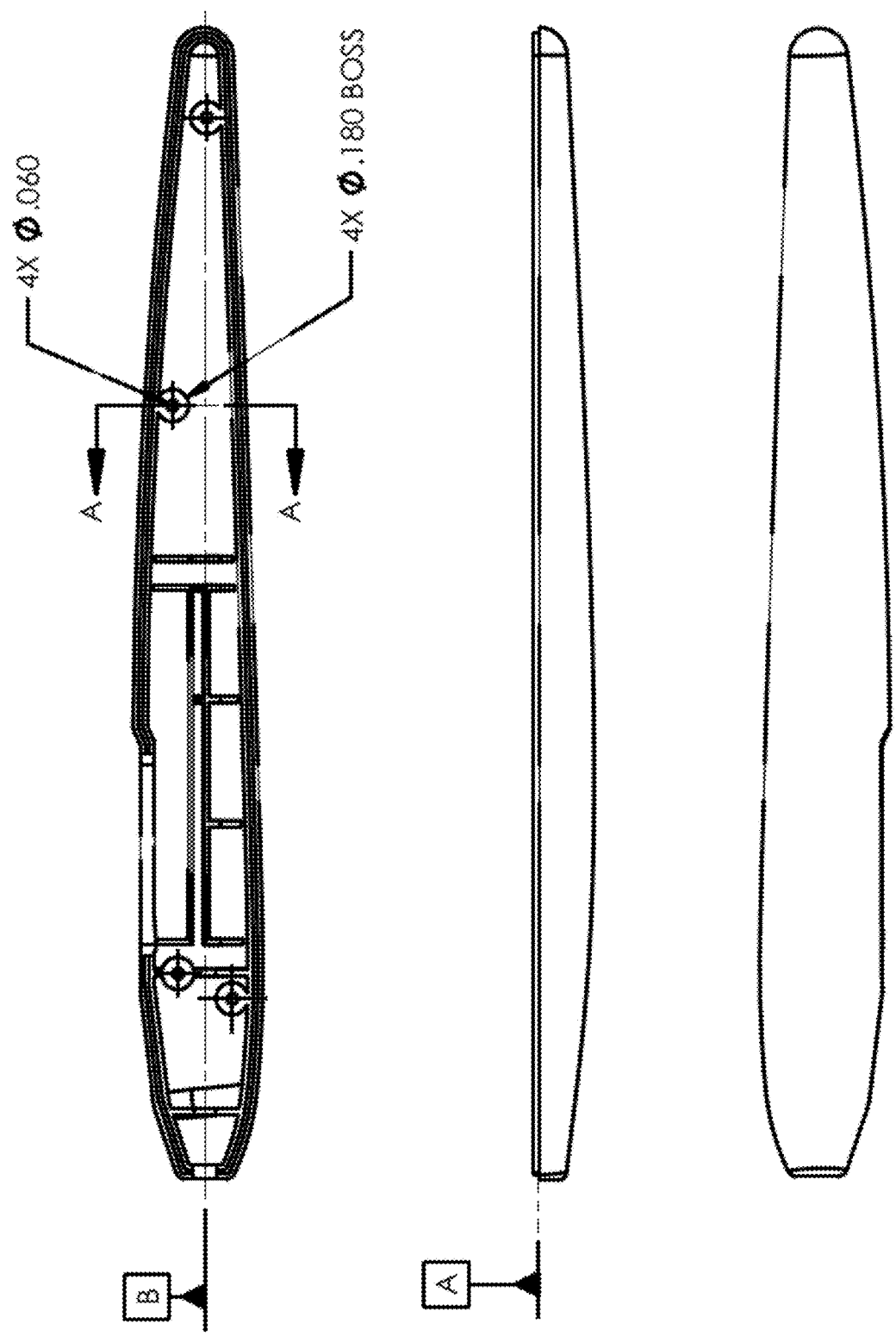
Figure 2G:
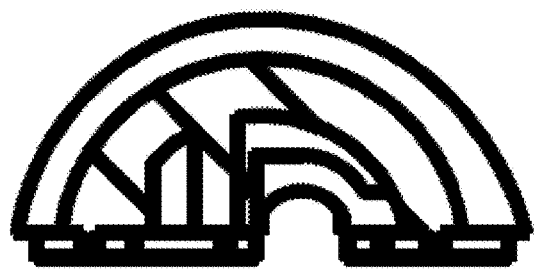

FIG. 1B illustrates the intraocular injector assembly 100 in use during an intraocular injection procedure. In various embodiments, the user (e.g., a healthcare provider) inserts the cannula needle 104 through the sclera of an eye 150 and into the posterior chamber 151. In various embodiments, the user may insert the cannula needle 104 in a manner to avoid the various structures of the anterior segment of the eye (e.g., cornea, iris, ciliary body, and/or lens). The healthcare provider may position the distal end 105 of the cannula needle 104 at a target location within the eye 150 and proceed to eject an implant (e.g., a solid therapeutic drug) at the target location by pushing the latch 108 forward with a finger (e.g., an index finger). Similar to FIG. 1B, FIG. 1C illustrates the intraocular injector assembly 100 in use during another injection procedure. In various embodiments, the user (e.g., a healthcare provider) inserts the cannula needle 104 through the sclera of an eye 150 and into the anterior chamber 152. In various embodiments, when inserting the injector into the anterior chamber 152, the healthcare provider may insert the cannula needle 104 parallel to the iris 153 so as not to damage the iris 153 or structures around the iris 153 (e.g., the lens capsule, the lens, etc.).

FIG. 1C illustrates a 3D model of an intraocular injector assembly 100 in accordance with an embodiment of the present disclosure. As shown in FIG. 1C, the housing 102 may include one or more apertures 103 into which a fixation mechanism (e.g., a screw) is inserted to thereby affix one part of the housing 102 to another part of the housing 102. In various embodiments, the housing parts may be joined without fixation mechanisms, such as by a snap-fit, welding, and/or bonding.

FIG. 2 illustrates a cross-section if an intraocular injector assembly 100 in accordance with an embodiment of the present disclosure. In various embodiments, the housing 102 defines an internal chamber 107, which may house at least a part of various components of the injector assembly 100, such as the cannula needle 104, the needle stop 106, the latch 108, and a pushrod 110 coupled to the latch 108. In various embodiments, as will be described in more detail below, the injector assembly includes a flexible arm 114 affixed to the cannula needle 104.

As shown in FIG. 2, the latch 108 is slidably disposed within a slot 109 formed in a surface (e.g., outer surface) of the housing and providing access to the internal chamber 107. In various embodiments, the latch 108 includes a seating portion that is configured to contact the user's finger during use. In various embodiments, the seating portion of the latch 108 may be ergonomically-designed for a particular finger of a user, such as an index finger. In various embodiments, the seating portion may include one or more surface features configured to improve grip of the finger and reduce the chance that the finger slips during use. In various embodiments, the surface features may include any suitable structure that increases the friction between the user's finger and the latch thereby preventing slippage of the finger off of the latch 108. In various embodiments, the seating portion may include a plurality of raised bumps. In various embodiments, the seating portion may include a plurality of raised bars.

In various embodiments, the latch 108 is coupled to a pushrod 110. In various embodiments, the pushrod 110 is disposed entirely within the housing 102. In various embodiments, the pushrod 110 is formed as a separate component from the latch 108. In various embodiments, the pushrod is formed as an integral component with the latch 108, i.e., both the latch 108 and the pushrod 110 are formed as one component. In various embodiments, at least a portion of the pushrod may extend into the distal opening of the cannula needle 104. In various embodiments, the distal-most end of the latch 108 may be proximal to the distal-most end of the pushrod 110. In this embodiment, the device may feel more comfortable to the user, as if they are holding a pen.

In various embodiments, the needle stop 106 may extend at least partially into the internal chamber 107 of the housing 102. In various embodiments, the needle stop 106 may be configured as a bushing. In various embodiments, the needle stop 106 may be laser welded to the cannula needle 104. In various embodiments, the needle stop 106 may be secured within the housing 102 by one or more alignment structures of the housing 102.

FIGS. 2B-2G illustrates various mechanical drawings of an intraocular injector housing in accordance with an embodiment of the present disclosure. In various embodiments, the housing 102 may be formed of two components 102a and 102b (e.g., halves). In various embodiments, the components 102a, 102b may be coupled together via an integral fastening element, such as a latch, hinge, and/or detent. In various embodiments, the components 102a, 102b may be coupled together via a mechanical fastener, such as a screw, rivet, pin, nail, etc. In various embodiments, the components 102a, 102b may be coupled together via a permanent joint, such as a weld (e.g., hot gas, vibration, ultrasonic, induction, dielectric, etc.) or bonding process (e.g., solvent, fusion, etc.).

Figure 3A:
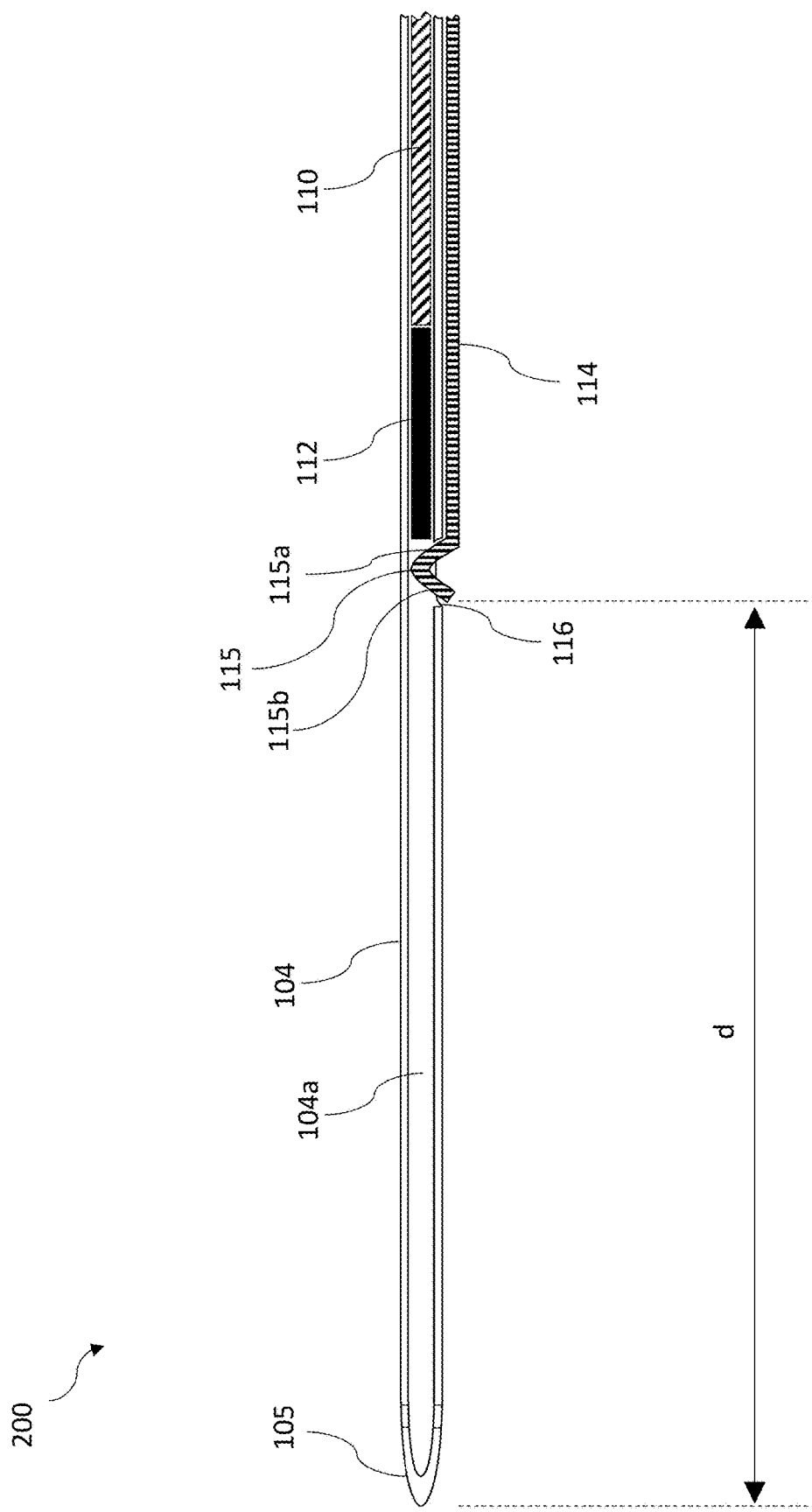
FIGS. 3A-3C illustrate a needle subassembly in accordance with an embodiment of the present disclosure.
Figure 3B:
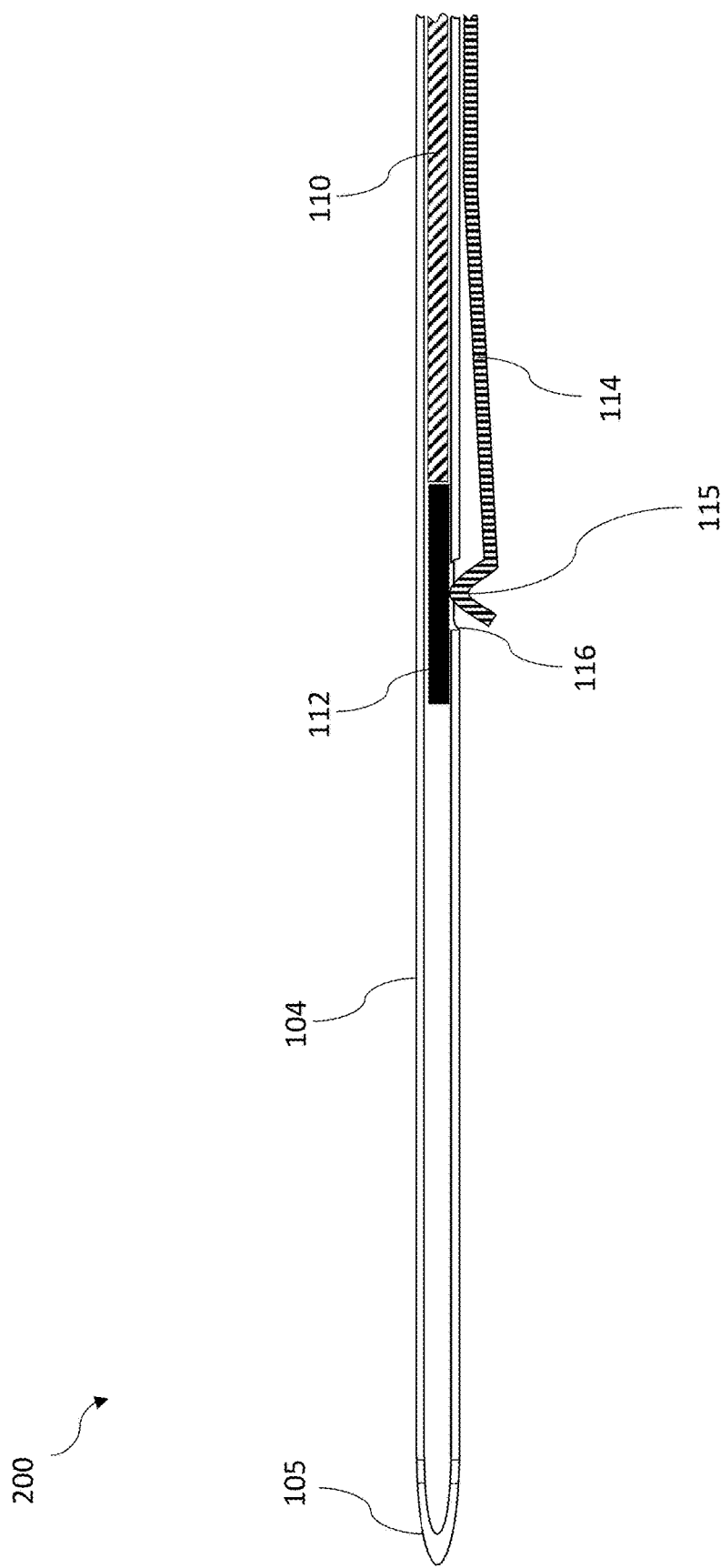
Figure 3C:
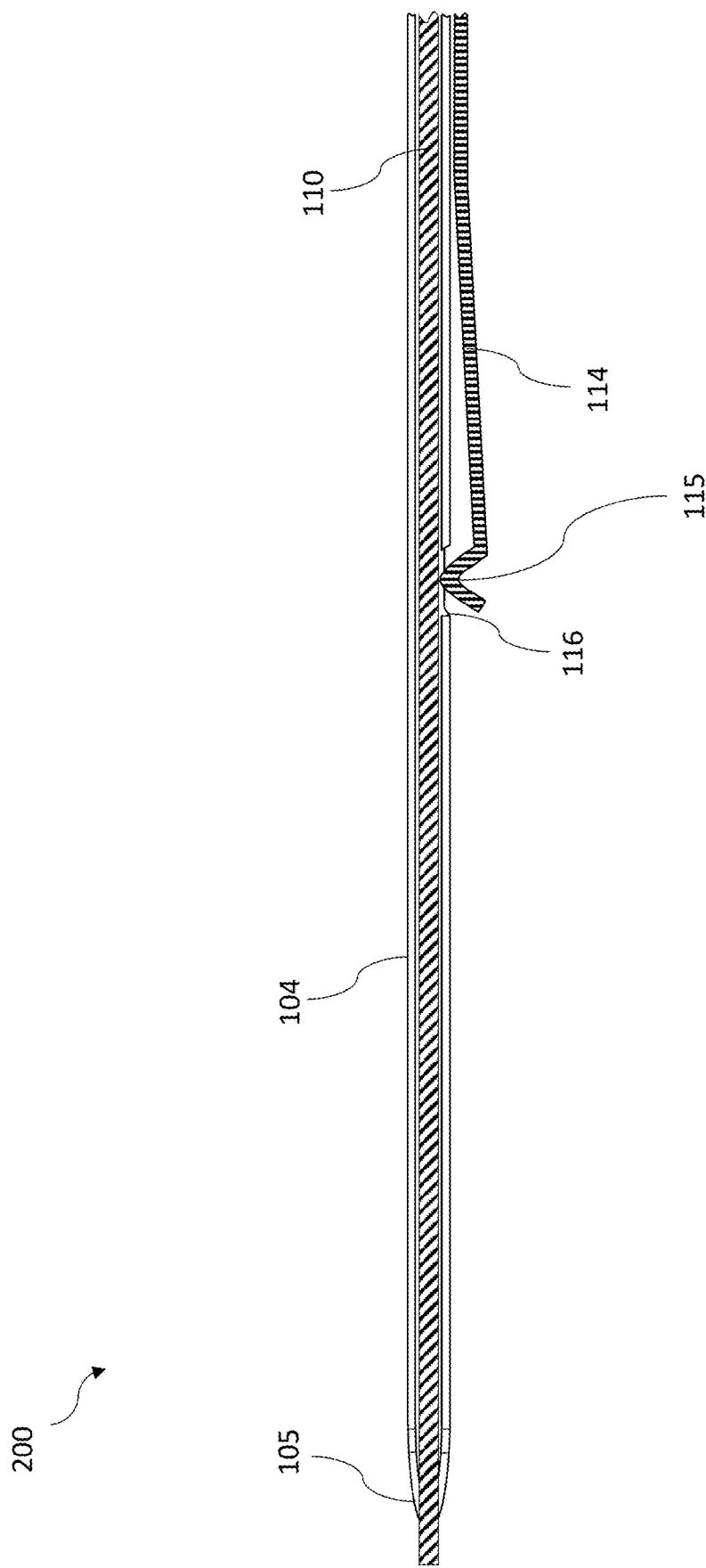
Figure 4A:
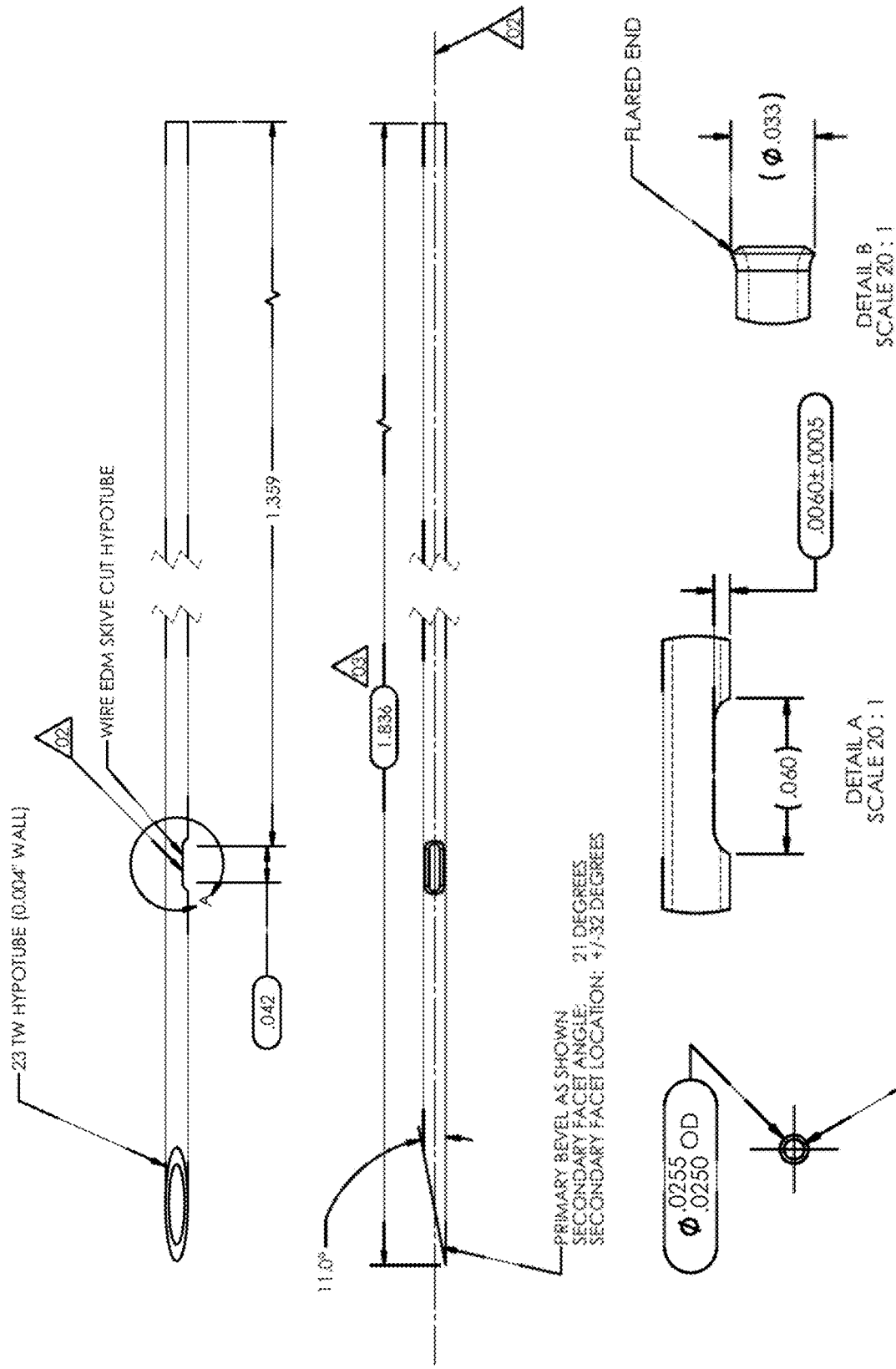
FIGS. 4A-4C illustrate various mechanical drawings of a needle subassembly in accordance with an embodiment of the present disclosure.

FIG. 3A-3C illustrate a needle subassembly 200 in accordance with an embodiment of the present disclosure. The needle subassembly 200 includes the cannula needle 104 having a beveled distal end 105, a cutout 116 disposed along the shaft of the cannula needle 104 at a distance d away from the distal end 105 of the cannula needle, an implant 112, and a pushrod 110. In various embodiments, the distanced may be about 5 mm to about 100 mm. Preferably the distanced may be about 10 mm to about 35 mm. As shown in FIG. 3A, the needle subassembly 200 includes a flexible arm 114 affixed (e.g. welded) to the cannula needle 104 at a proximal end thereof; this can prohibit longitudinal movement of the flexible arm relative to the needle 104. The flexible arm 114 includes a hook 115 having a first portion 115a extending through the cutout 116 and into a lumen 104a of the cannula needle 104, and a second portion 115b extending outwardly towards, and in some embodiments through, the cutout 116. The cutout can be EDM skive cut to have rounded or chamfered edges (as best shown in FIG. 4A) to prevent or inhibit risk of the hook 115 from engaging or "snagging" against the needle 104 when being displaced out of the lumen. Likewise, in some embodiments the edge or end of the hook can be formed with a rounded or bulbous shape to prevent snagging. In some embodiments a coating can be applied to the hook to reduce the frictional forces exhibited when the payload contacts (and displaces) the hook during deployment. This can be advantageous in that it reduces risk of damage to the payload. In various embodiments, the hook 115 may include a V-shape.

In various embodiments, the first portion 115a of the hook 115 may be configured such that a (longitudinally applied) force of an implant 112 causes the hook 115 to displace out of the cutout 116 thereby allowing the implant 112 and the pushrod 110 to pass (over the hook 115, as oriented in FIG. 3A) through the lumen 104a. The displacing force can be applied such that the hook is gradually displaced outside of the lumen 104a. In some embodiments, the apex of the hook is displaced completely outside of the lumen 104a. In various embodiments, the force necessary to displace the hook 115 is below (e.g., greater than a factor of safety of 1) a threshold that could damage the implant 112. In various embodiments, the angle of the first portion 115a is about 10 degrees to about 75 degrees from the horizontal (i.e., longitudinal axis of the cannula needle). Preferably, the angle of the first portion 115a is about 65 degrees from the horizontal. In various embodiments, an angle between the first portion 115a and the second portion 115b is about 30 degrees to about 70 degrees. Preferably, the angle between the first portion 115a and the second portion 115b is about 50 degrees. In various embodiments, the second portion 115b may extend up to the outer surface of the cutout 116. In various embodiments, the second portion 115b may extend no further, or less than the outer surface of the cutout 116. In various embodiments, as shown in FIG. 3A, the second portion 115b may extend beyond the outer surface of the cutout 116. In various embodiments, the cutout 116 may be formed as a skive cut.

FIG. 3B shows a first step in ejecting the implant 112 where a user slides the latch 108 forward with their finger thereby causing the pushrod 110 to contact the proximal end of the implant 112 and advance the implant 112 through the lumen 104a. As the implant 112 advances distally through the lumen 104a, the distal end of the implant 112 contacts the first portion 115a of the hook 115. Because the first portion 115a is disposed at a shallow angle relative to the horizontal, the force of the implant 112 contacting the first portion 115a displaces the hook 115 away from the lumen 104a and out of the cutout 116. In FIG. 3B, the implant is directly under the hook 115 and the flexible arm 114 is acting as a cantilever beam (fixed at its proximal end) bending along its length. In various embodiments, the flexible arm 114 may undergo elastic deformation. In various embodiments, the flexible arm 114 may undergo plastic deformation (e.g., for a single-use device).

In various embodiments, a cushion may be provided between the pushrod 110 and the implant 112 to thereby protect the implant 112 from any potential damage. In various embodiments, the cushion may be placed at the proximal end of the implant 112, the distal end of the implant 112, or coat the implant 112. In various embodiments, the cushion may include a liquid, a gas, a gel, and/or a lubricant.

FIG. 3C shows the last step in ejecting the implant 112 out of the cannula needle 104 where the latch 108 has translated about its maximum distance and the implant 112 is ejected from the distal end 105 of the cannula needle 104. In particular, the pushrod 110 extends beyond the distal end 105 of the cannula needle 104 to ensure that the implant 112 is ejected therefrom. As shown in FIG. 3C, the pushrod 110 continues to force the hook 115 out of the cutout 116. In various embodiments, the pushrod 110 may include a pit (not shown) at a predetermined position along its length corresponding to a maximum translation of the latch 108. In various embodiments, the pit may be sized such that the hook 115 of the flexible arm 114 snaps back into the cutout 116 and into the pit to thereby prevent retraction of the pushrod (e.g., for a single-use device). In various embodiments, the snapping motion of the hook 115 into the pit may provide an audible sound for the user to provide an indication to the user that the maximum translation has been reached and that the implant 112 has been ejected from the cannula needle 104.

In various embodiments, the implant may be a therapeutic agent. In various embodiments, the implant may be a drug. In various embodiments, the implant may be a solid. In various embodiments, the drug may include at least one of: a steroid, an anti-vascular endothelial growth factor (anti-VEGF), a prostaglandin, a beta blocker, an alpha-2 agonist, cholinergic, carbonic anhydrase inhibitor, nucleoside reverse transcriptase inhibitor (NRTI), tyrosine kinase inhibitor, and rho kinase inhibitor. In various embodiments, the steroid may include dexamethasone. In various embodiments, the anti-VEGF may include bevacizumab, ranibizumab, or aflibercept. In various embodiments, the prostaglandin may be latanoprost, latanoprostene, tafluprost, bimatoprost, or travoprost. In various embodiments, the beta blocker may be timolol maleate, timolol hemihydrate, metipranolol, betaxolol, or levobunolol. In various embodiments, the alpha-2 agonist may be brimonidine tartrate or apraclonidine. In various embodiments, the cholinergic may be pilocarpine or carbachol. In various embodiments, the carbonic anhydrase inhibitor may be methazolamide, dorzolamide, brinzolamide, or acetazolamide. In various embodiments, the rho kinase inhibitor may be netarsudil. For example, the drug may be a solid dexamethasone implant.

Figure 4B:
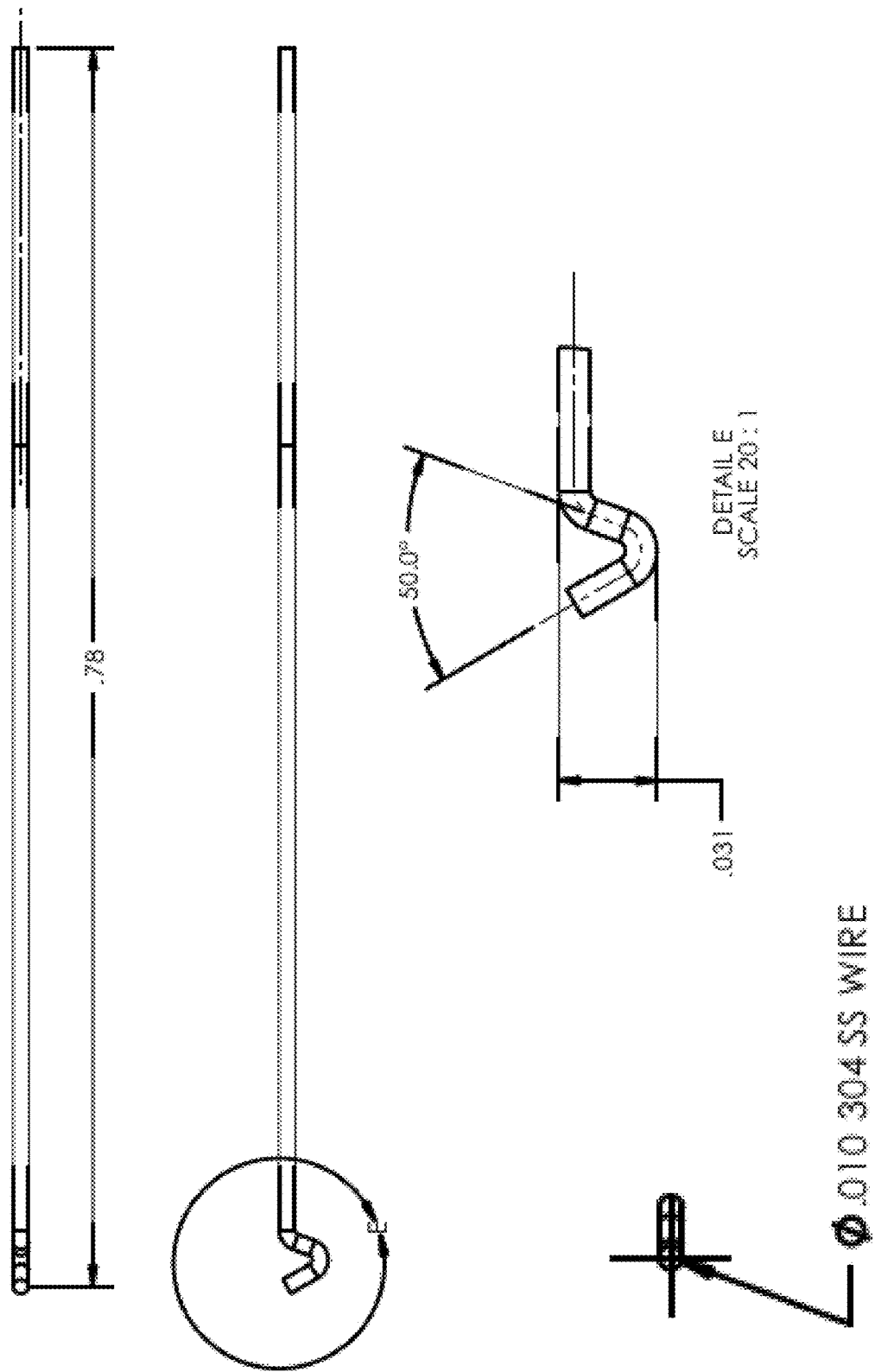
Figure 4C:
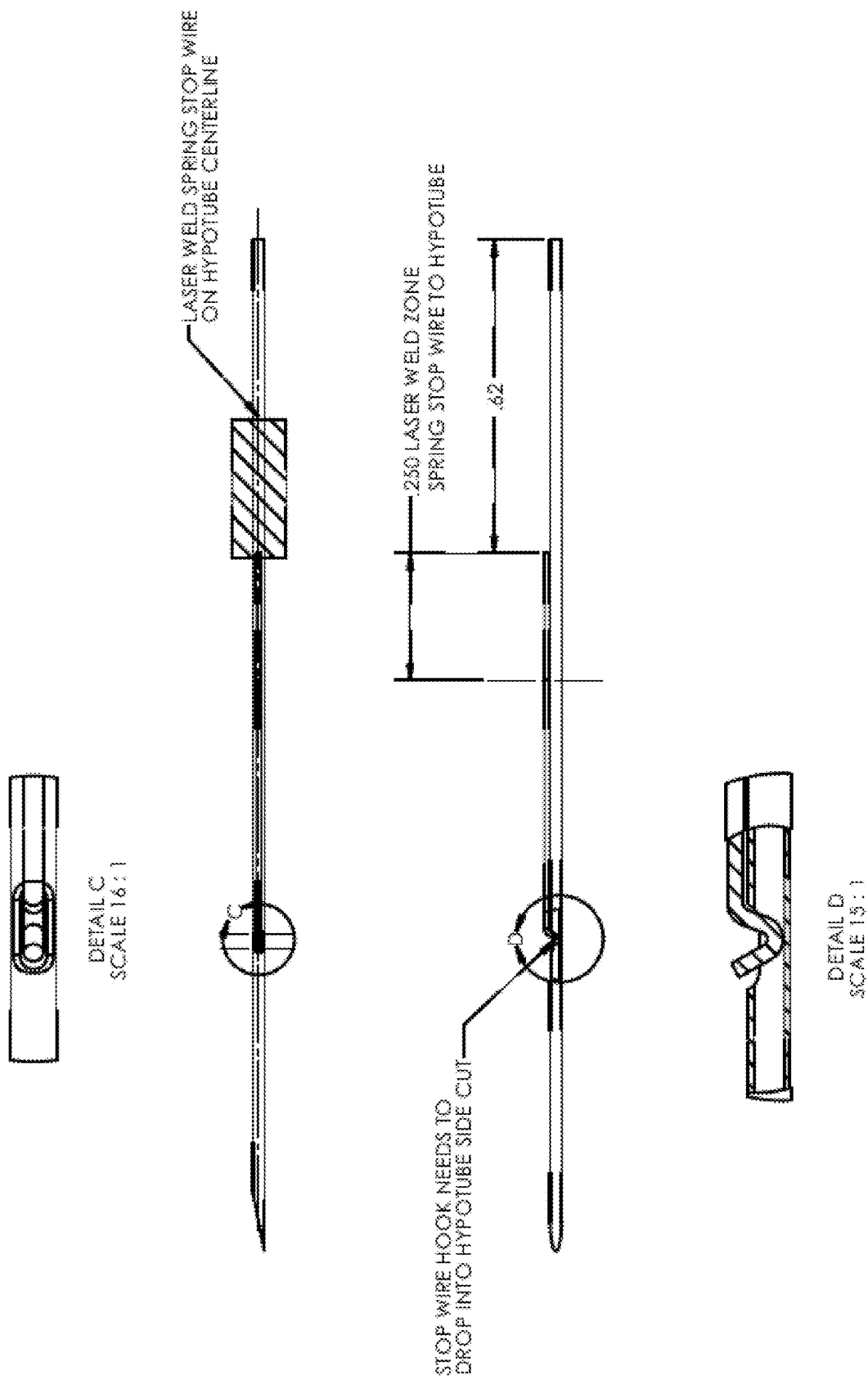
Figure 5A:
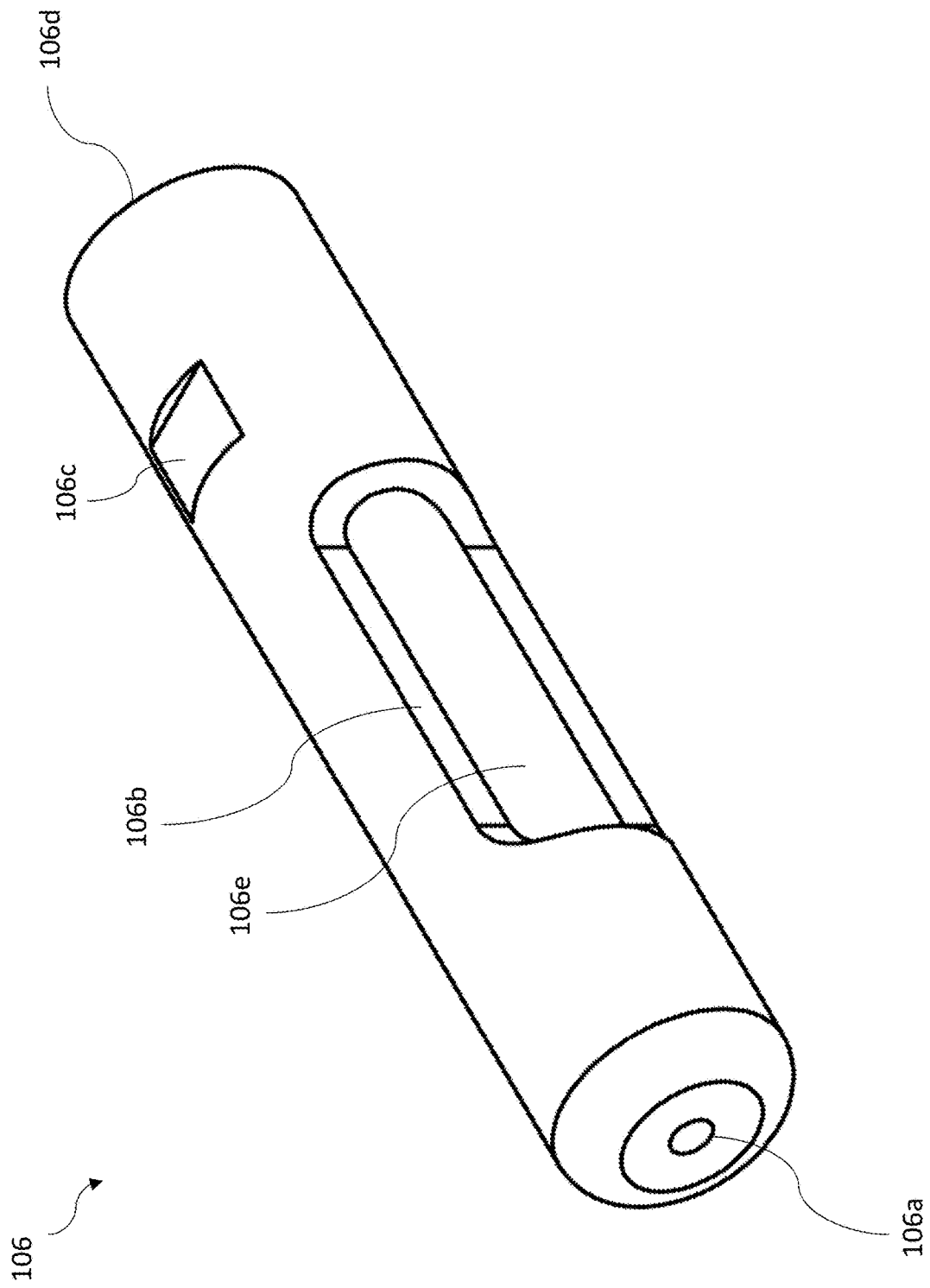
FIGS. 5A-5D illustrate various mechanical drawings of a needle stop in accordance with an embodiment of the present disclosure.
Figure 5B:
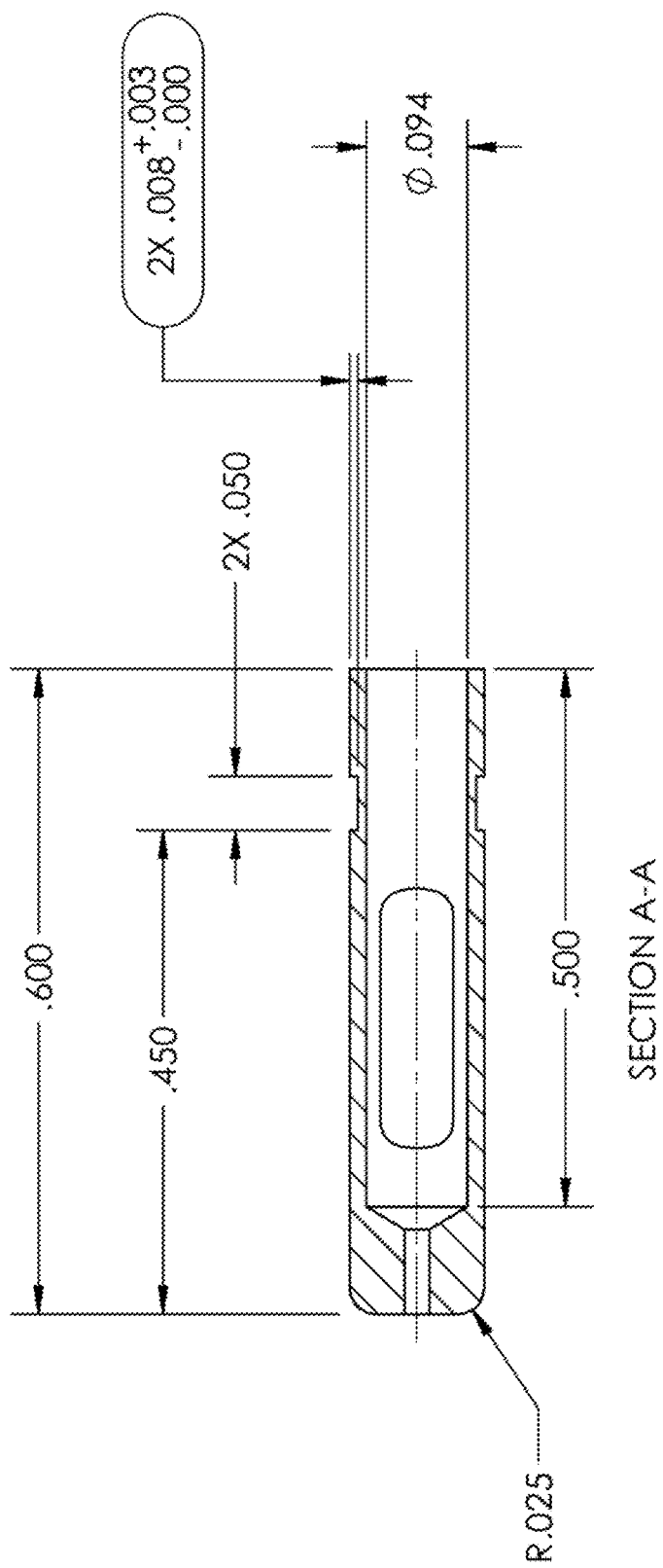
Figure 5C:
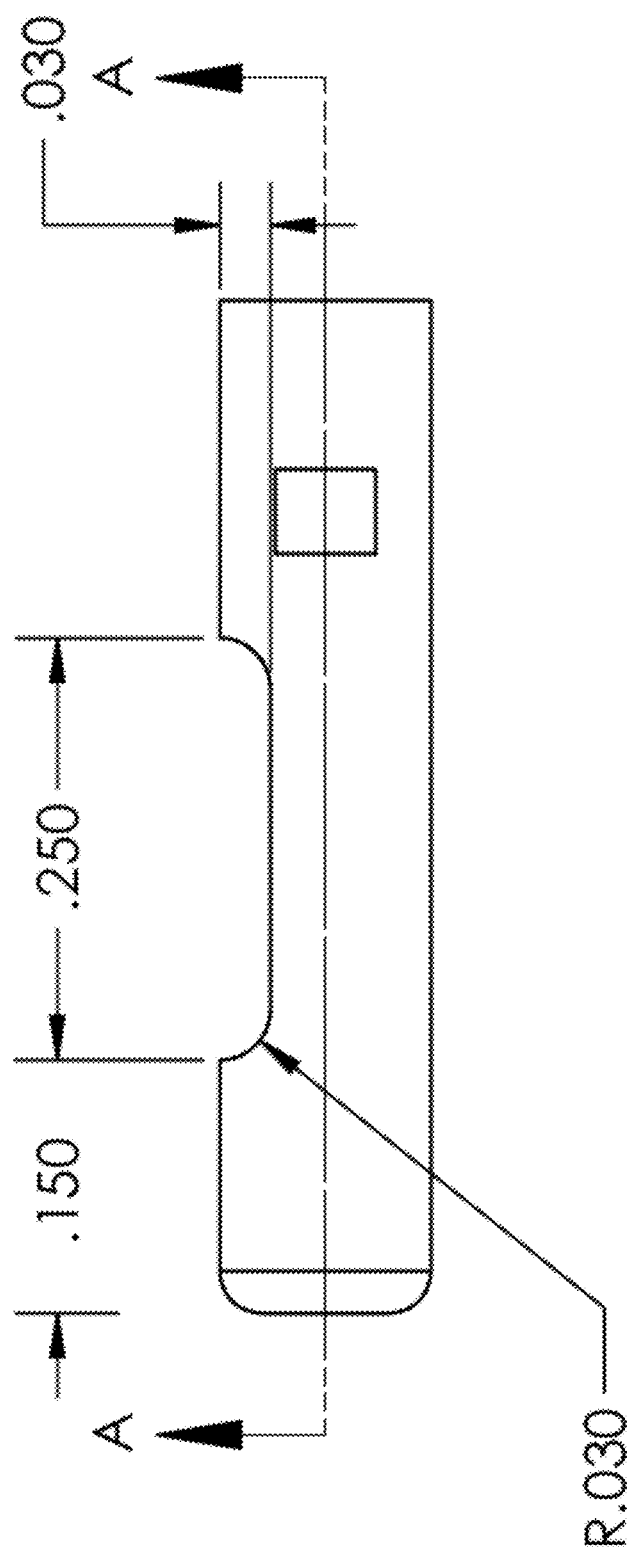
Figure 5D:
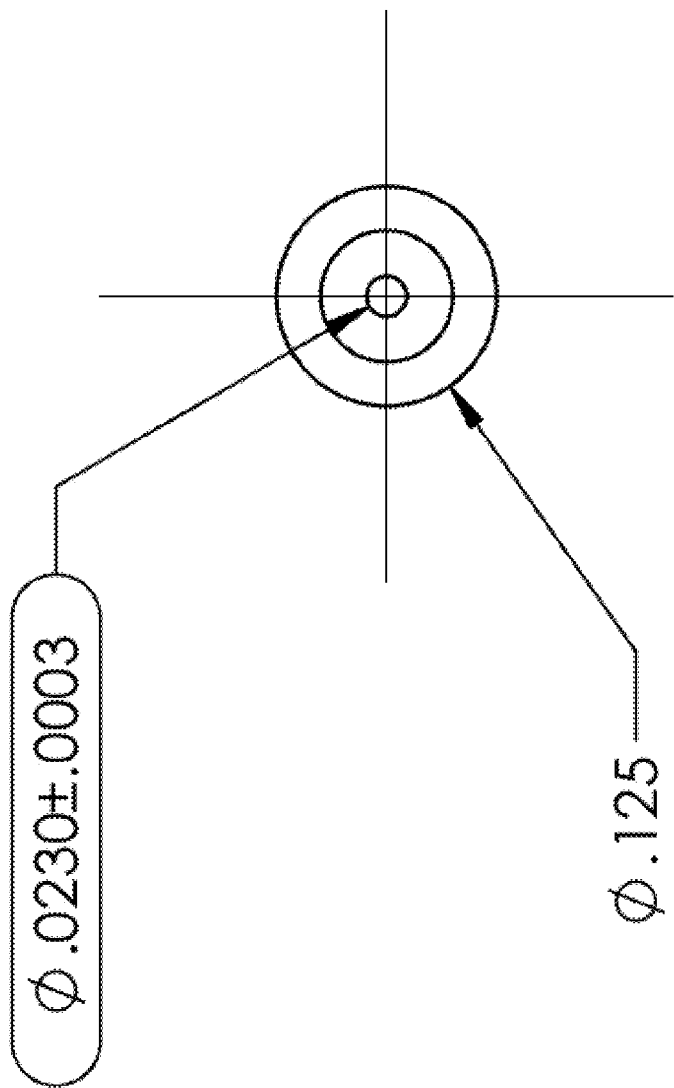

FIG. 4A-4C illustrate various mechanical drawings of a needle subassembly in accordance with an embodiment of the present disclosure.

FIGS. 5A-5D illustrate various mechanical drawings of a needle stop 106 in accordance with an embodiment of the present disclosure. In various embodiments, the needle stop may be substantially cylindrical-shaped. In various embodiments, the needle stop 106 may include a distal bore 106a configured to receive the cannula needle 104. In various embodiments, the distal bore may have a diameter that is substantially similar (e.g., slightly larger than or equal) to the outer diameter of the cannula needle 104. In various embodiments, the needle stop may be laser welded to the cannula needle 104 at the distal bore. In various embodiments, the needle stop 106 may include a cutout 106b. In various embodiments, the cutout 106b of the needle stop 106 may align substantially with the cutout 116 of the cannula needle 104. In various embodiments, the cutout 106b of the needle stop 106 may be sized (e.g., a larger cutout) to allow the motion of the flexible arm 114 and hook 115 to be displaced out of the cutout 116 of the cannula needle 104. In various embodiments, the needle stop may include one or more positioning grooves 106c configured to align the needle stop 106 within the housing 102. In various embodiments, the needle stop 106 may having a proximal bore 106d and a central chamber 106e having a diameter that is larger than the diameter of the distal bore. In various embodiments, the cutout 106b may be formed as a skive cut.

Figure 6A:
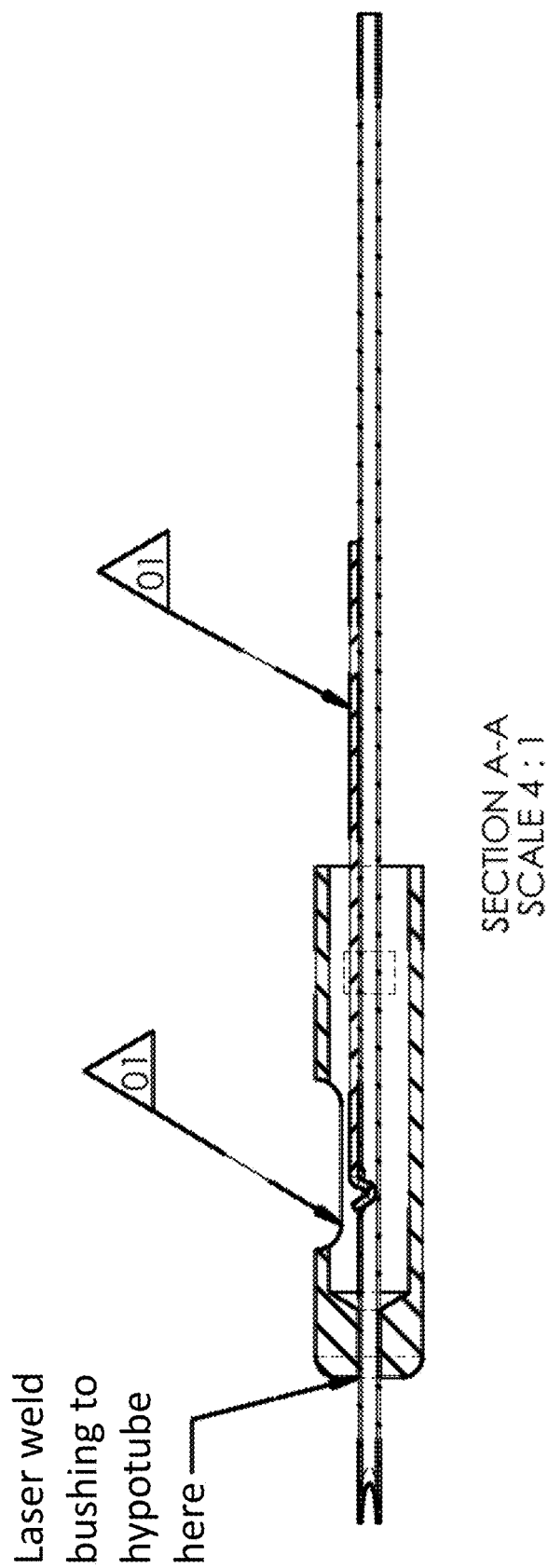
Figure 6B:
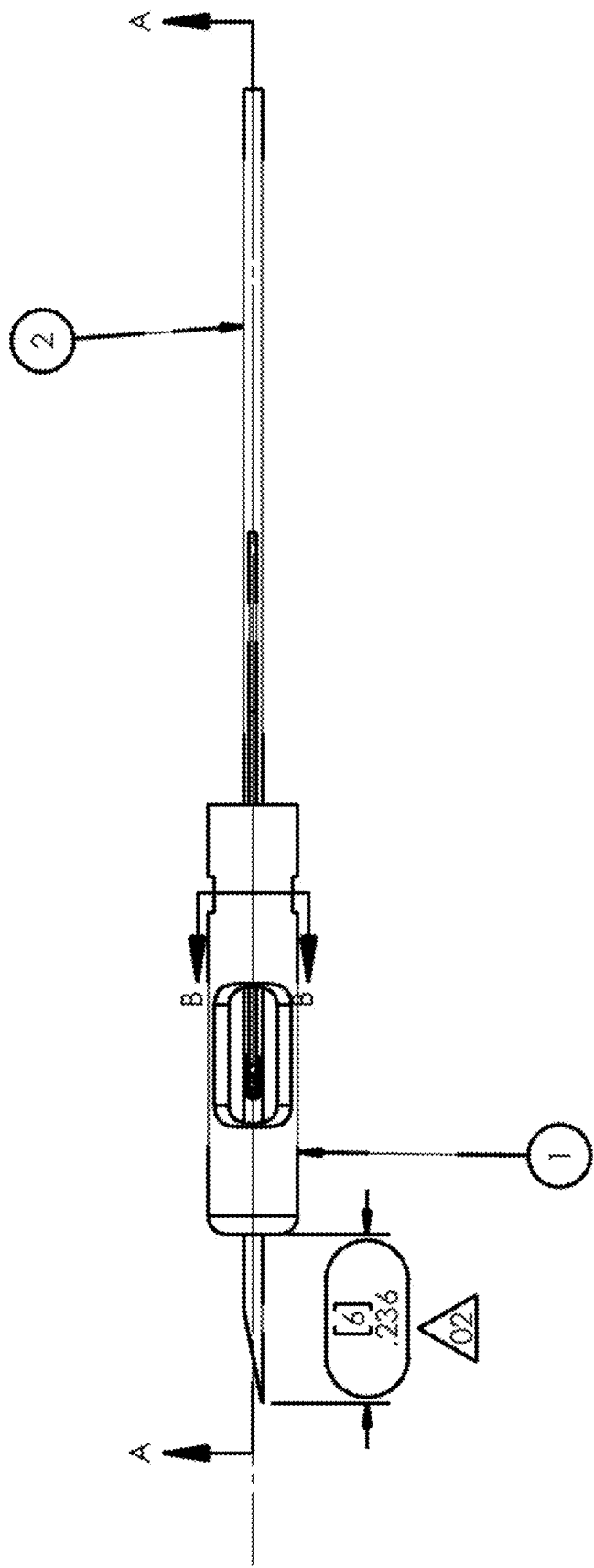

FIG. 6A-6C illustrates a various mechanical drawings of a needle subassembly with needle stop in accordance with an embodiment of the present disclosure.

Figure 7A:
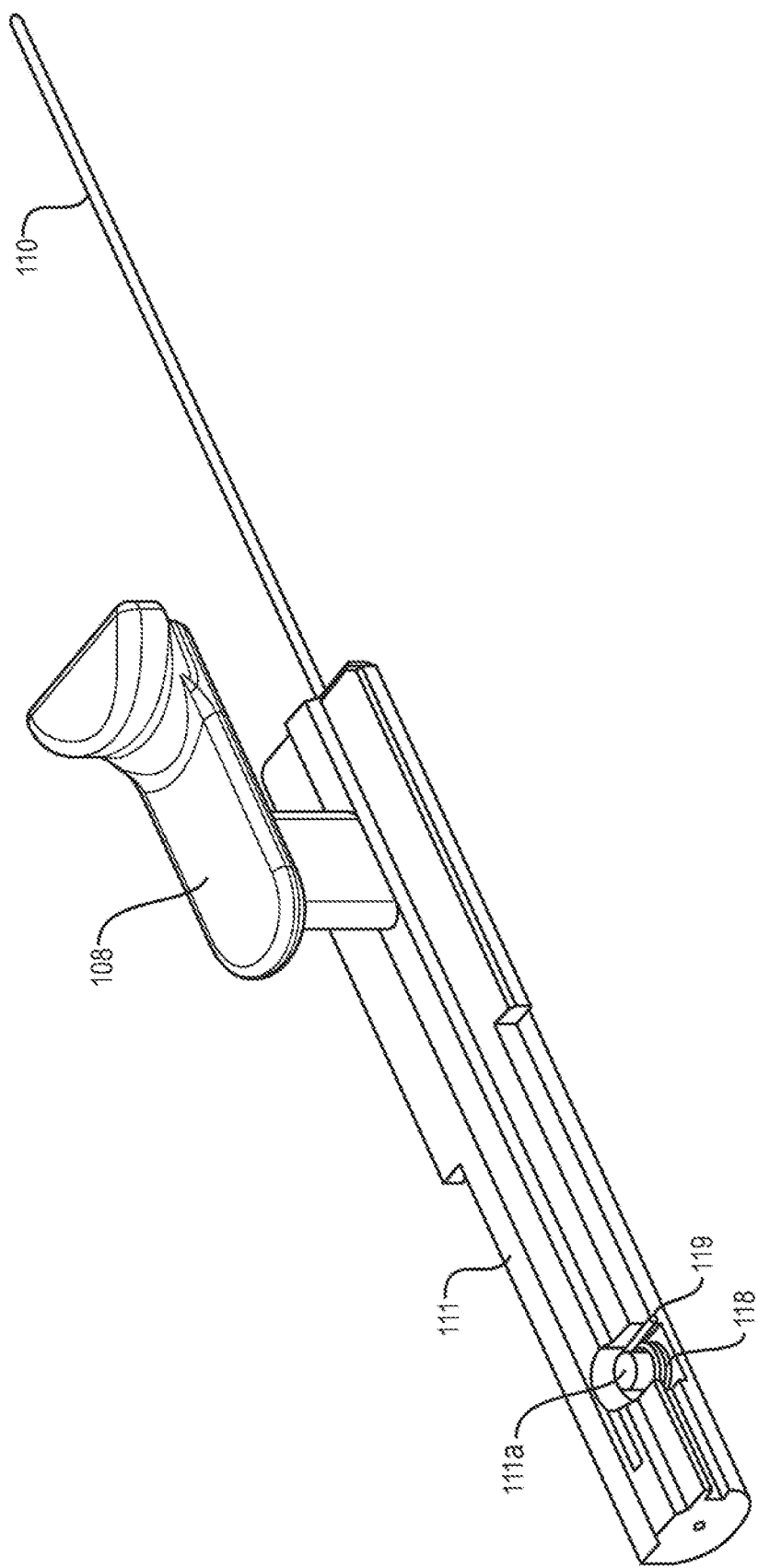
FIGS. 7A-7B illustrate an exemplary pushrod and latch in accordance with an embodiment of the present disclosure.
Figure 7B:
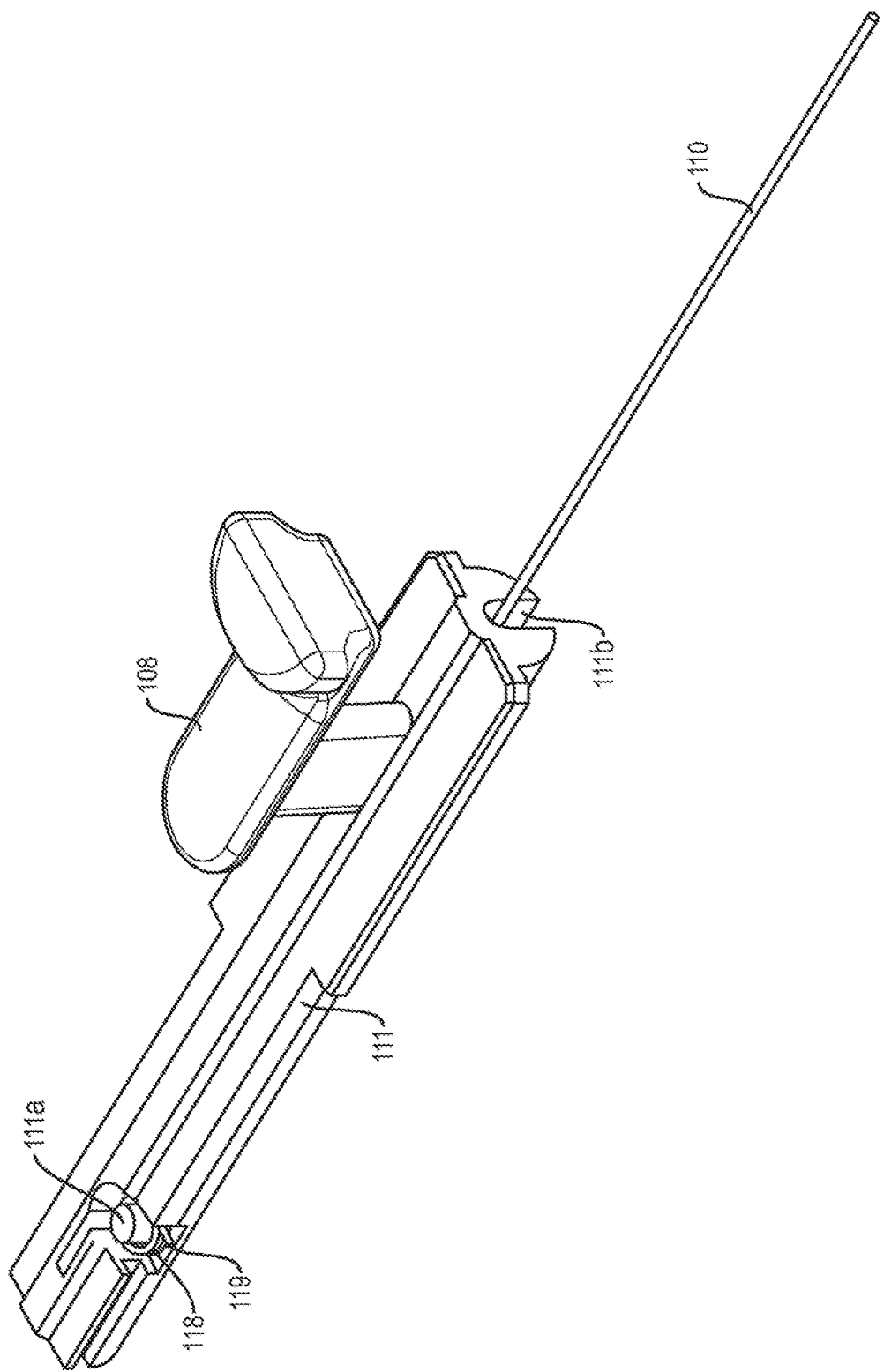
Figure 7C:
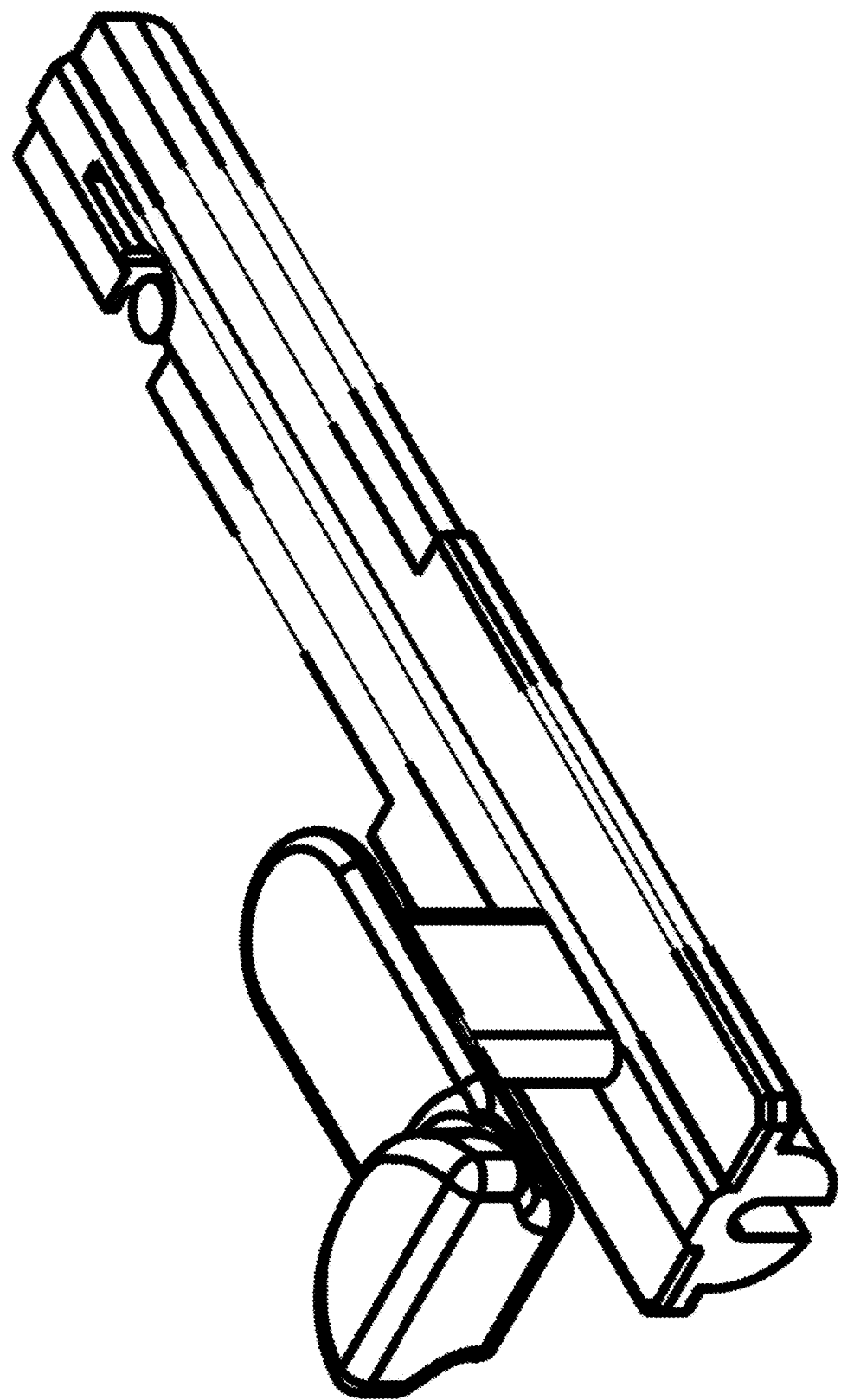
FIGS. 7C-7F illustrate mechanical drawings of an exemplary pushrod and latch in accordance with an embodiment of the present disclosure.
Figure 7D:
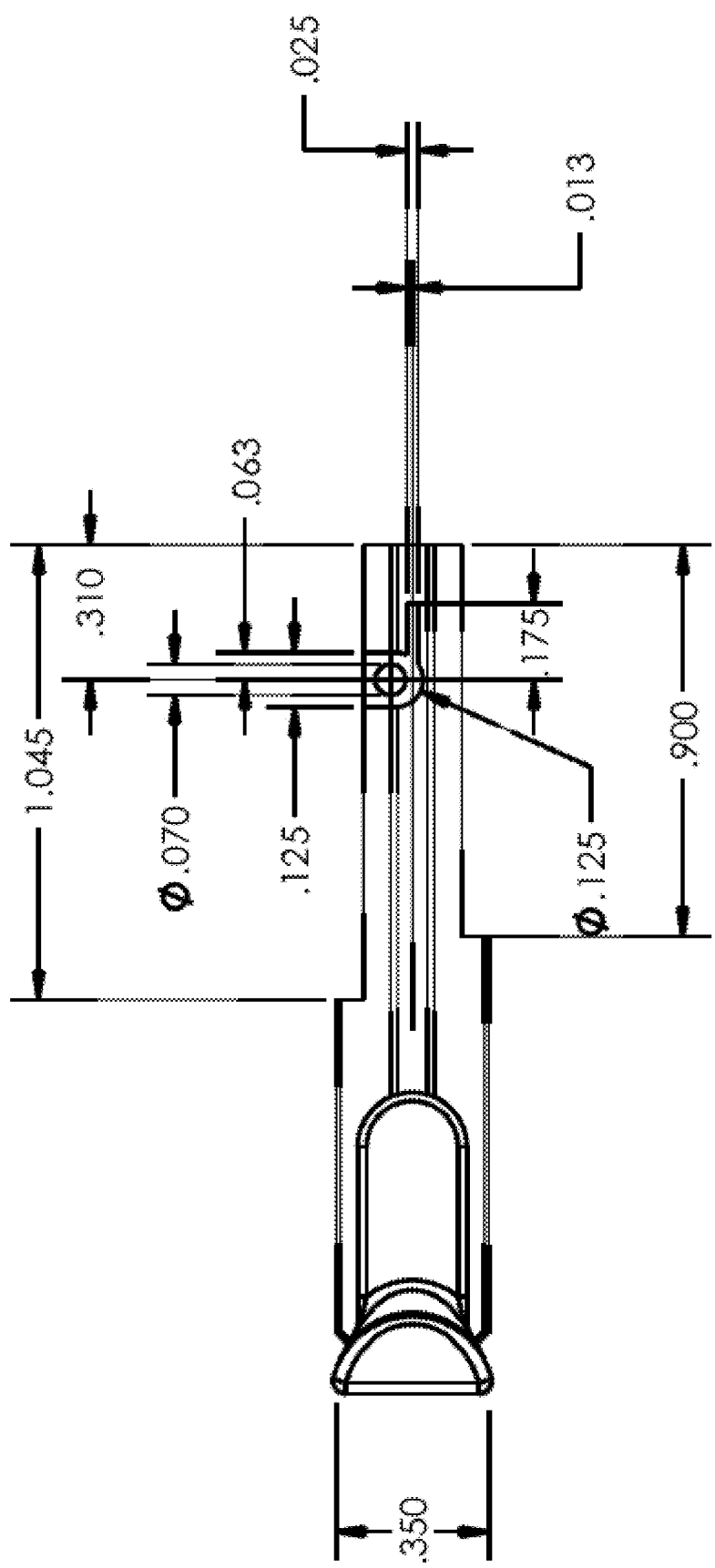
Figure 7E:
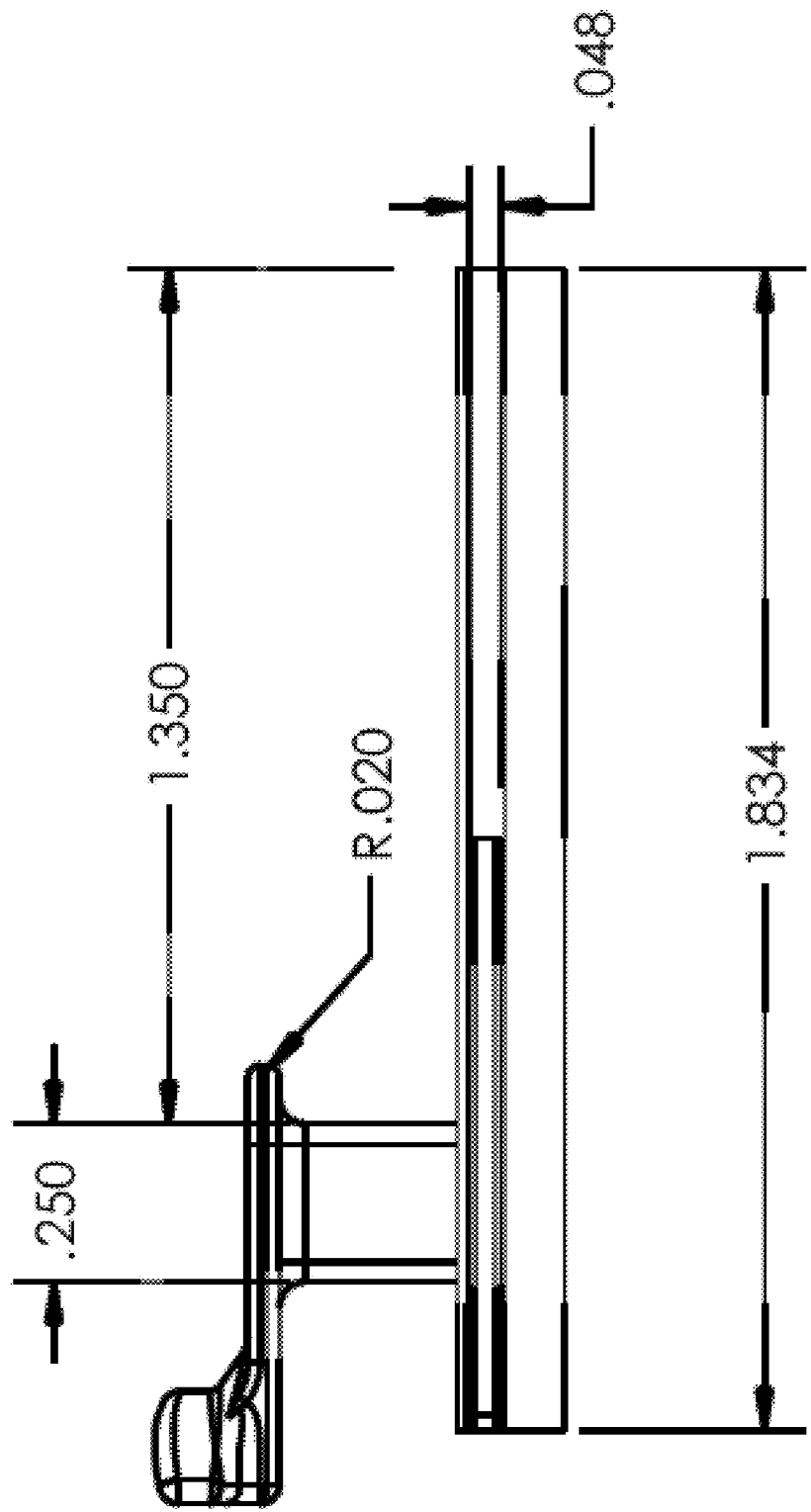
Figure 7F:
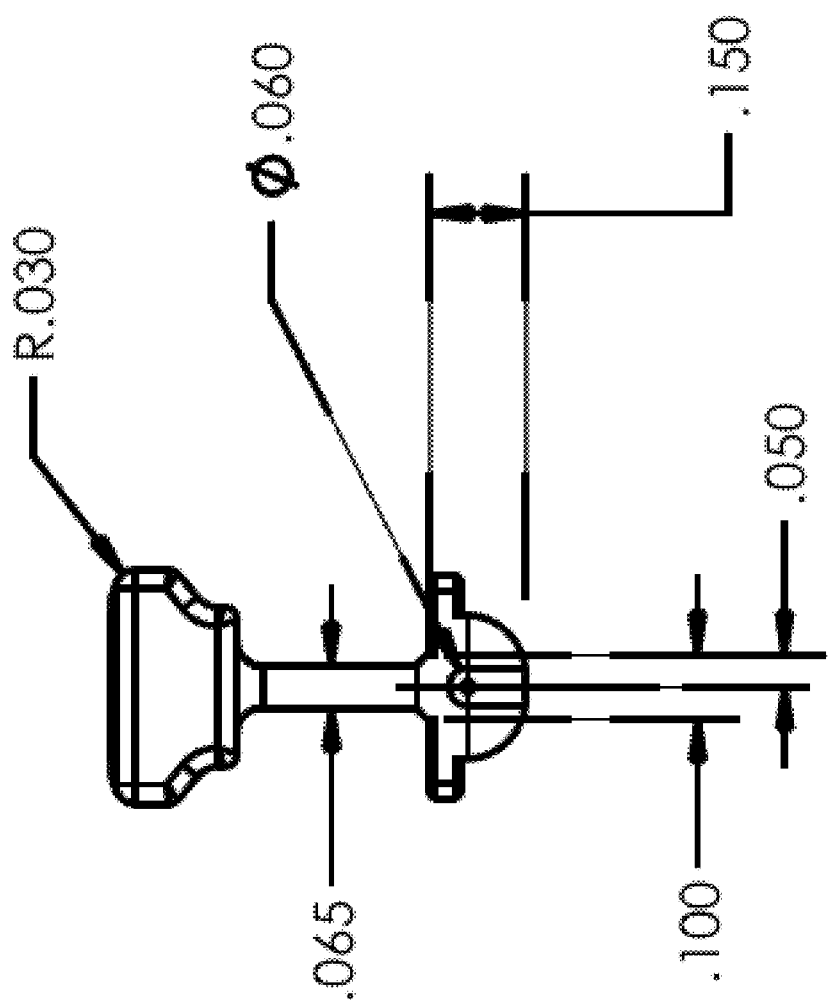

FIGS. 7A-7B illustrate an exemplary pushrod and latch in accordance with an embodiment of the present disclosure. FIGS. 7C-7F illustrate mechanical drawings of an exemplary pushrod 110 and latch 108 in accordance with an embodiment of the present disclosure. In various embodiments, the latch 108 may be coupled to the pushrod 110 via a body 111. In various embodiments, the body 111 may include a central bore 111b out of which the pushrod 110 may extend. In various embodiments, at least a portion of the central bore 111b may include slot. In various embodiments, the proximal end of the pushrod 110 is affixed to a protrusion 111a on the body 111. In various embodiments, the proximal end of the pushrod 110 may be coiled around the protrusion 111a thereby creating a coil 118. In various embodiments, the coil 118 may include an end 119 extending outward from the body 111. In various embodiments, the end 119 of the coil 118 may extend perpendicularly outward from the body 111. In various embodiments, the end 119 of the coil 118 may extend at an acute angle (i.e., less than 90 degrees) away from the body 111. In various embodiments, the end 119 may extend beyond the outer surface of the body 111 such that the end 119 may engage a one-way catch on the body 111 (e.g., inside surface of the body 111) while the body is permitted to slide within the housing unobstructed but for the end 119 of the coil 118. In various embodiments, the end 119 of the coil 118 may extend at an obtuse angle (i.e., greater than 90 degrees) away from the body 111. In various embodiments, the protrusion 111a may be disposed within a recessed portion of the body 111. In various embodiments, the central bore 111b may extend to the recessed portion of the body 111. In various embodiments, the protrusion 111a and/or the coil 118 may prevent the latch 108 from being pulled backwards after use thereby permitting only single use of the injector. In various embodiments, the end 119 of the coil 118 may catch on an interior portion of the injector housing 102 thereby preventing the latch 108 from being retracted after the latch 108 is advanced beyond a predetermined position (e.g., the position of the latch that causes the implant to be fully ejected). In various embodiments, the end 119 of the coil 118 may be advanced past a one-way catch inside the housing 102 that permits the end 119 to be advanced forward, but after the end 119 translates past the one-way catch in the forward direction, the end 119 is not capable of translating past the one-way catch in the reverse direction.

In various embodiments, the cannula needle 104 may be made of a metal. In various embodiments, the metal may be stainless steel. In various embodiments, the flexible arm may be made of a metal. In various embodiments, the metal may be stainless steel. In various embodiments, the needle stop 106 may be made of a metal. In various embodiments, the metal may be stainless steel.

What is claimed is:

1. An injector assembly comprising:
    a housing defining an internal chamber, the housing having a proximal end and a distal end including a distal opening, the housing having a slot on an external surface thereof between the proximal end and distal end;
    a cannula needle having a proximal end disposed within the housing and extending at least partially through the distal opening to a distal end, the cannula needle having a lumen extending therethrough, the cannula needle having a distal bevel at the distal end and a proximal opening at the proximal end, the cannula needle having a cutout on an outer surface further comprising a bushing disposed around the cutout, wherein the bushing comprises a cutout that is substantially aligned with the cutout of the cannula needle;
    a flexible arm having a proximal end and a distal end, the proximal end of the flexible arm affixed to the outer surface of the cannula needle and the distal end of the flexible arm having a hook, wherein the hook is disposed within the cutout;
    a pushrod slidably disposed within the lumen, the pushrod extending at least partially through the distal end of the cannula needle; and
    a latch slidably disposed in the slot of the housing, the latch coupled to the pushrod such that translation of the latch causes translation of the pushrod.

2. The injector assembly of claim 1, further comprising an implant disposed proximal to the hook and distal to the pushrod.

3. The injector assembly of claim 2, wherein the implant comprises a therapeutic agent, the therapeutic agent comprising at least one of: a steroid, an anti-vascular endothelial growth factor, a prostaglandin, a beta blocker, a nucleoside reverse transcriptase inhibitor (NRTI), a tyrosine kinase inhibitor, or an alpha-2 agonist.

4. The injector assembly of claim 2, wherein the hook is configured to be displaced upon the pushrod applying a force to the implant thereby partially or fully displacing the hook from the cutout.

5. The injector assembly of claim 1, further comprising a needle stop disposed at the distal opening, wherein the needle stop extends at least partially out of the distal opening.

6. The injector assembly of claim 1, wherein a distal-most end of the latch is proximal to a distal-most end of the pushrod.

7. The injector assembly of claim 1, wherein the hook comprises a first portion extending into the lumen and a second portion extending towards the cutout.

8. The injector assembly of claim 7, wherein the second portion extends beyond the cutout.

9. The injector assembly of claim 7, wherein the hook comprises a V-shape.

10. The injector assembly of claim 7, wherein an angle between the first portion and the second portion is between 10 degrees and 90 degrees.

11. The injector assembly of claim 1, wherein the bushing comprises the needle stop.

12. The injector assembly of claim 1, wherein the bushing comprises a distal opening having a first diameter substantially the same as an outer diameter of the cannula needle, and a proximal opening having a second diameter that is larger than the first diameter.

13. The injector assembly of claim 1, wherein the bushing is affixed to the cannula needle.

14. The injector assembly of claim 1, wherein the latch comprises a body having a projection at a distal end of the body, and the pushrod is coupled to the projection.

15. The injector assembly of claim 14, wherein the pushrod is coupled to the projection via a coil.

16. A method of inserting an implant into an eye, the method comprising:
    providing an injector assembly of claim 1;
    inserting the distal end of the cannula needle into an eye;
    positioning the cannula needle at a target location within the eye;
    sliding the latch towards the distal end of the housing to thereby advance the pushrod against the implant, displacing the hook, until the implant is ejected from the needle cannula.

* * * * *